United States Patent
Geri et al.

(10) Patent No.: US 11,547,499 B2
(45) Date of Patent: Jan. 10, 2023

(54) DYNAMIC AND INTERACTIVE NAVIGATION IN A SURGICAL ENVIRONMENT

(71) Applicant: Surgical Theater LLC, Mayfield Village, OH (US)

(72) Inventors: Alon Yakob Geri, Orange Village, OH (US); Mordechai Avisar, Highland Heights, OH (US)

(73) Assignee: SURGICAL THEATER, INC., Los Angeles, CA (US)

( * ) Notice: Subject to any disclaimer, the term of this patent is extended or adjusted under 35 U.S.C. 154(b) by 352 days.

(21) Appl. No.: 15/301,833

(22) PCT Filed: Apr. 6, 2015

(86) PCT No.: PCT/US2015/024487
§ 371 (c)(1),
(2) Date: Oct. 4, 2016

(87) PCT Pub. No.: WO2015/154069
PCT Pub. Date: Oct. 8, 2015

(65) Prior Publication Data
US 2017/0035517 A1    Feb. 9, 2017

Related U.S. Application Data

(60) Provisional application No. 61/975,330, filed on Apr. 4, 2014.

(51) Int. Cl.
*G06T 19/20* (2011.01)
*A61B 34/00* (2016.01)
(Continued)

(52) U.S. Cl.
CPC .............. *A61B 34/25* (2016.02); *A61B 34/20* (2016.02); *A61B 90/37* (2016.02); *G06F 3/0488* (2013.01);
(Continued)

(58) Field of Classification Search
CPC ........ A61B 2034/105; A61B 2034/256; A61B 2560/0487; A61B 34/20; A61B 34/25;
(Continued)

(56) References Cited

U.S. PATENT DOCUMENTS

| | | |
|---|---|---|
| 5,595,703 A | 1/1997 | Swaelens et al. |
| 5,768,134 A | 6/1998 | Swaelens et al. |

(Continued)

FOREIGN PATENT DOCUMENTS

| | | |
|---|---|---|
| CN | 1720561 A | 1/2006 |
| CN | 1973780 A | 6/2007 |

(Continued)

OTHER PUBLICATIONS

Montgomery, K. et al; Studies in Health Technology and Informatics; "Spring: A General Framework for Collaborative, Real-time Surgical Simulation"; 2002, vol. 85, pp. 296-303.

(Continued)

*Primary Examiner* — Sultana M Zalalee
(74) *Attorney, Agent, or Firm* — Bodi Law LLC

(57) ABSTRACT

A system and method for converting medical images of a particular patient into high resolution, 3D dynamic and interactive images interacting with medical tools including medical devices by coupling a model of tissue dynamics and tool characteristics to the patient specific imagery for simulating a medical procedure in an accurate and dynamic manner. The method includes a tool to add and/or to adjust the dynamic image of tissues and ability to draw and add geometric shapes on the dynamic image of tissues. The (Continued)

system imports the 3D surgery plan (craniotomy, head position, approach etc.). The surgeon establishes multiple views, rotates and interacts with the navigation image to see behind pathology and vital structures. The surgeon can make structures such as tumors, vessels and tissue transparent to improve visualization and to be able to see behind the pathology. The System can warn on proximity of tools to specific anatomical structure.

28 Claims, 22 Drawing Sheets
(20 of 22 Drawing Sheet(s) Filed in Color)

(51) Int. Cl.
| | |
|---|---|
| G09B 23/28 | (2006.01) |
| A61B 34/20 | (2016.01) |
| A61B 90/00 | (2016.01) |
| G06F 3/04845 | (2022.01) |
| G06F 3/0488 | (2022.01) |
| G06T 11/20 | (2006.01) |
| G06F 3/048 | (2013.01) |
| A61B 34/10 | (2016.01) |

(52) U.S. Cl.
CPC ........ *G06F 3/04845* (2013.01); *G06T 11/203* (2013.01); *G06T 19/20* (2013.01); *G09B 23/285* (2013.01); *G09B 23/286* (2013.01); *A61B 2034/105* (2016.02); *A61B 2034/256* (2016.02); *A61B 2560/0487* (2013.01); *G06F 3/048* (2013.01); *G06T 2200/24* (2013.01); *G06T 2210/41* (2013.01); *G06T 2219/2004* (2013.01); *G06T 2219/2016* (2013.01); *G06T 2219/2021* (2013.01)

(58) Field of Classification Search
CPC ..... A61B 90/37; G06F 3/048; G06F 3/04845; G06F 3/0488; G06T 11/203; G06T 19/20; G06T 2200/24; G06T 2210/41; G06T 2219/2004; G06T 2219/2016; G06T 2219/2021
See application file for complete search history.

(56) References Cited

U.S. PATENT DOCUMENTS

| | | | |
|---|---|---|---|
| 5,826,206 A | 10/1998 | Nemeth | |
| 6,037,927 A | 3/2000 | Rosenberg | |
| 6,113,395 A | 9/2000 | Hon | |
| 6,847,336 B1 | 1/2005 | Lemelson et al. | |
| 6,857,878 B1 | 2/2005 | Chosack et al. | |
| 6,863,536 B1 | 3/2005 | Fisher et al. | |
| 6,939,138 B2 | 9/2005 | Chosack et al. | |
| 7,101,383 B1 | 9/2006 | Van Ess | |
| 7,261,565 B2 | 8/2007 | Chosack et al. | |
| 7,616,730 B2 | 11/2009 | Flohr | |
| 8,311,791 B1 | 11/2012 | Avisar | |
| 8,504,136 B1 | 8/2013 | Sun et al. | |
| 8,831,924 B2* | 9/2014 | Avisar ................ G09B 23/28 703/11 |
| 9,788,905 B2 | 10/2017 | Avisar | |
| 10,056,012 B2* | 8/2018 | Geri .................... G06F 19/00 |
| 2001/0046935 A1 | 11/2001 | Okamura | |
| 2002/0059284 A1 | 5/2002 | Bronstein et al. | |
| 2002/0077542 A1* | 6/2002 | Vilsmeier ............. A61C 1/084 600/424 |
| 2003/0109070 A1* | 6/2003 | Hosoya ................. G06T 7/41 438/14 |
| 2004/0253572 A1 | 12/2004 | Chosack et al. | |
| 2005/0032028 A1 | 2/2005 | Chosack et al. | |
| 2005/0159759 A1* | 7/2005 | Harbaugh .......... A61B 17/3211 606/130 |
| 2006/0036167 A1 | 2/2006 | Shina | |
| 2006/0082542 A1 | 4/2006 | Morita et al. | |
| 2006/0085175 A1 | 4/2006 | Hartlep et al. | |
| 2006/0116576 A1* | 6/2006 | McGee .................. A61B 6/12 600/434 |
| 2006/0184006 A1* | 8/2006 | Chen ..................... A61B 6/12 600/416 |
| 2006/0281971 A1 | 12/2006 | Sauer | |
| 2007/0129626 A1* | 6/2007 | Mahesh ................ A61B 34/76 600/407 |
| 2007/0134637 A1 | 6/2007 | Bronstein et al. | |
| 2007/0141543 A1 | 6/2007 | Grund-Pedersen | |
| 2007/0236491 A1* | 10/2007 | Hundley ................ A61B 5/055 345/418 |
| 2007/0248261 A1 | 10/2007 | Zhou et al. | |
| 2008/0033410 A1* | 2/2008 | Rastegar ................ A61B 18/20 606/9 |
| 2009/0018808 A1 | 1/2009 | Bronstein et al. | |
| 2009/0187393 A1 | 7/2009 | Van Lierde et al. | |
| 2009/0248184 A1* | 10/2009 | Steingart ................ A61C 1/082 700/98 |
| 2009/0311655 A1 | 12/2009 | Karkanias et al. | |
| 2009/0326556 A1* | 12/2009 | Diolaiti ............... A61B 1/00009 606/130 |
| 2010/0009314 A1 | 1/2010 | Tardieu et al. | |
| 2010/0069919 A1* | 3/2010 | Carls .................. A61B 17/7083 606/130 |
| 2010/0092904 A1 | 4/2010 | Esposti et al. | |
| 2010/0149174 A1* | 6/2010 | Nakao .................... A61B 6/466 345/419 |
| 2010/0161076 A1 | 6/2010 | Pallari | |
| 2010/0178644 A1 | 7/2010 | Meglan et al. | |
| 2010/0191088 A1 | 7/2010 | Anderson et al. | |
| 2010/0217336 A1 | 8/2010 | Crawford et al. | |
| 2010/0299101 A1* | 11/2010 | Shimada ................ G09B 23/28 702/150 |
| 2010/0305928 A1 | 12/2010 | Cohen et al. | |
| 2011/0015649 A1* | 1/2011 | Anvari .................. A61B 34/20 606/130 |
| 2011/0054295 A1* | 3/2011 | Masumoto ............. A61B 5/055 600/407 |
| 2011/0112549 A1* | 5/2011 | Neubach ................ A61B 8/485 606/130 |
| 2011/0144658 A1* | 6/2011 | Wenderow ............. A61B 6/481 606/130 |
| 2011/0164029 A1* | 7/2011 | King .................... G06F 3/04883 345/419 |
| 2011/0194742 A1* | 8/2011 | Buelow .................... G06T 7/11 382/128 |
| 2011/0236868 A1 | 9/2011 | Bronstein et al. | |
| 2011/0238395 A1 | 9/2011 | Kubota et al. | |
| 2011/0282686 A1* | 11/2011 | Venon .................... G16H 80/00 705/3 |
| 2011/0301982 A1* | 12/2011 | Green, Jr. .............. G06Q 10/06 705/3 |
| 2012/0041446 A1* | 2/2012 | Wong .................. A61B 17/1703 606/96 |
| 2012/0058457 A1 | 3/2012 | Savitsky | |
| 2012/0143268 A1* | 6/2012 | Burroughs ............. A61B 34/20 606/86 R |
| 2012/0182291 A1* | 7/2012 | Rawat ..................... G06T 17/00 345/419 |
| 2012/0280988 A1* | 11/2012 | Lampotang .......... G09B 23/285 345/419 |
| 2013/0047103 A1 | 2/2013 | Avisar | |
| 2013/0073310 A1* | 3/2013 | Awdeh .................. G06Q 50/22 705/2 |
| 2013/0090554 A1* | 4/2013 | Zvuloni ............. A61B 10/0241 600/424 |
| 2013/0176336 A1* | 7/2013 | Hannula ................ A61B 5/0042 345/633 |
| 2013/0189663 A1* | 7/2013 | Tuchschmid .......... G09B 23/28 434/262 |
| 2013/0211792 A1* | 8/2013 | Kang ..................... G09B 23/30 703/1 |

(56) References Cited

U.S. PATENT DOCUMENTS

| | | |
|---|---|---|
| 2013/0267838 A1 | 10/2013 | Fronk et al. |
| 2014/0088941 A1 | 3/2014 | Banerjee et al. |
| 2014/0107471 A1* | 4/2014 | Haider .............. A61B 1/3132 600/424 |
| 2014/0176661 A1 | 6/2014 | Smurro et al. |
| 2014/0267220 A1* | 9/2014 | Mehta .................. G06T 19/20 345/419 |
| 2014/0275760 A1 | 9/2014 | Lee |
| 2015/0100066 A1* | 4/2015 | Kostrzewski ........ A61B 34/30 606/130 |
| 2016/0005169 A1* | 1/2016 | Sela .................... A61B 5/0066 382/131 |
| 2016/0312598 A1* | 10/2016 | Samuel ................. G05B 11/36 |
| 2018/0092698 A1 | 4/2018 | Chopra et al. |

FOREIGN PATENT DOCUMENTS

| | | |
|---|---|---|
| CN | 102354345 A | 2/2012 |
| EP | 1 395 194 A1 | 3/2004 |
| EP | 3 146 715 A1 | 3/2017 |
| EP | 3 280 344 A2 | 2/2018 |
| JP | 2006509238 A | 3/2006 |
| JP | 2006223374 | 8/2006 |
| JP | 2010131047 | 6/2010 |
| JP | 2014522248 | 9/2014 |
| JP | 2014525764 | 10/2014 |
| WO | 9610949 | 4/1996 |
| WO | WO9610949 A1 | 4/1996 |
| WO | WO 02/100284 A1 | 12/2002 |
| WO | 2004029908 A1 | 4/2004 |
| WO | 2004051603 A1 | 6/2004 |
| WO | WO2004051603 A1 | 6/2004 |
| WO | WO 2008/076079 | 6/2008 |
| WO | 2009059716 A1 | 5/2009 |
| WO | WO2009059716 A1 | 5/2009 |
| WO | 2009094621 A2 | 7/2009 |
| WO | 2010030523 A1 | 3/2010 |
| WO | WO2010106532 A1 | 9/2010 |
| WO | 2010132606 A1 | 11/2010 |
| WO | 2012/033739 A1 | 3/2012 |
| WO | 2012135653 A1 | 10/2012 |
| WO | 2013177520 A1 | 11/2013 |
| WO | WO 2015/008470 A2 | 1/2015 |
| WO | 2015154069 A1 | 10/2015 |

OTHER PUBLICATIONS

Qin, J et al; Studies in Health Technology and Informatics; "An Adaptive Framework Using Cluster-Based Hybrid Architecture for Enhancing Collaboration in Surgical Simulation"; 2007, vol. 125, pp. 367-372.

Joanna Leng; Scientific Examples of Virtual Reality and Visualization Applications; Manchester Research Center for Computational Science; Mar. 2001; part "Surgical Simulation".

M.A. Padilla et al., Computer Simulation of Prostate Surgery; Universidad Nacional Automoma de Mexico; Oct. 15, 2007.

Neurosurg vol. 93; Relevant Pages: pp. 355-369 and Figures 3, 4, 6 and 8; Date of Issuance: Aug. 31, 2000; Title of Article: "Simulation of the surgical manipulation involved in clipping a basilar artery aneurysm: concepts of virtual clipping"; Author and Publisher: Toru Koyama, M.D. et al.; Department of Neurosurgery, Shinshu University School of Medicine Matsumoto, Japan.

MedGadget (Surgical Navigation Advanced Platform (SNAP) for Intra-Op Visualization of Patient's Brain, https://www.medgadget.com/2014/07 /surg i cal-n avigation-advanced-platfor msnap-for-intra-op-visual izati on-of-patients-brain. ht ml, Jul. 3, 2014).I.

Reitinger et al. "Liver Surgery Planning using Virtual Reality" IEEE Computer Graphics and Applications.

PCT International Search Report; International Application No. PCT/US2015/024487; Applicant: Surgical Theater LLC; International Filing Date: Apr. 6, 2015; Date of Actual Completion of International Search: May 13, 2015; dated May 21, 2015.

Bornik A et al: "Computer Aided Liver Surgery Planni ng: An Augmented Reality Approach" Visual Communications and Image Processing; vol. 5029, Feb. 15, 2003, pp. 395-406.

Reitinger, et al: "Liver Surgery Planning Using Virtual Reality"; Virtual and Augmented Reality Supported Similators; IEEE Computer Society; Nov./Dec. 2006.

* cited by examiner

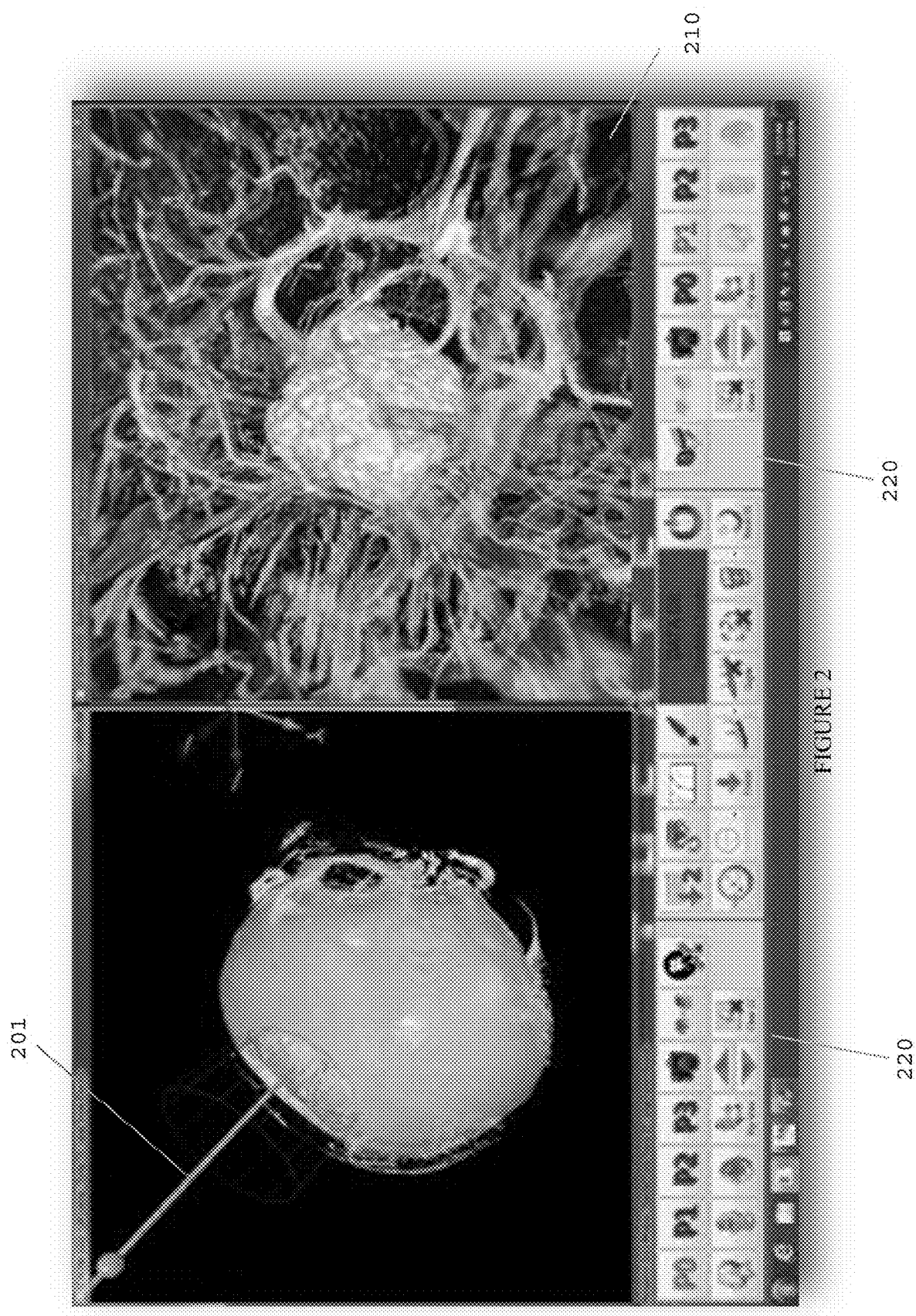

DYNAMIC AND INTERACTIVE NAVIGATION IN A SURGICAL ENVIRONMENT

CROSS-REFERENCES TO RELATED APPLICATIONS

This application is the national stage of International Application Serial No. PCT/US2015/024487 filed on Apr. 6, 2015, which claims the benefit of priority to U.S. Provisional Application Ser. No. 61/975,330 which was filed on Apr. 4, 2014, the entire disclosures of which are incorporated herein by reference.

BACKGROUND

This application relates generally to a system and method for displaying surgical procedures in a surgical environment to aid in the surgery. More specifically, this application relates to a system and method for converting static/still medical images of an actual surgical patient into dynamic and interactive images interacting with medical tools (such as, e.g., surgical tools, probes, and/or implantable medical devices) by coupling a model of tissue dynamics to patient specific imagery during a surgical procedure. The interacting with the medical tools come to fruition with the proximity warning, proximity warning is a mechanism for providing continues indication and warning for proximity of tools to specific anatomical structure.

Surgeons lack a surgical tool that would provide them with a realistic visual images of a surgical patient where realistic physical tissue properties are displayed together with the medical tools (such as, e.g., surgical tools, probes, and/or implantable medical devices) in a 3d display. A surgical tool that encompasses: (i) realistic "life-like" 2D and/or 3D display of the patient-specific area of surgery (for example—aneurysm); (ii) modeling of the local patient-specific area of surgery geometry and physical properties; (iii) interface enabling manipulation of the patient-specific area of surgery model and display surgical actions such as cutting, shifting and clamping; and (iv) interface to provide feedback cues to the surgeon: and give 3d navigation in a real-time that provide warning for proximity of tools to specific anatomical structure.

SUMMARY

Generally provided are example systems and methods for converting medical images of a particular patient into high resolution, 3D dynamic and interactive images interacting with medical tools including medical devices by coupling a model of tissue dynamics and tool characteristics to the patient specific imagery for simulating a medical procedure in an accurate and dynamic manner. The method includes a tool to add and/or to adjust the dynamic image of tissues and ability to draw and add geometric shapes on the dynamic image of tissues. The system imports the 3D surgery plan (craniotomy, head position, approach etc.). The surgeon establishes multiple views, rotates and interacts with the navigation image to see behind pathology and vital structures. The surgeon can make structures such as tumors, vessels and tissue transparent to improve visualization and to be able to see behind the pathology. The System can warn on proximity of tools to specific anatomical structure.

Also are a plurality of example embodiments, including, but not limited to, a modeling system for performing a medical procedure on a particular patient, comprising: a display; an image generator including specialized software executing on a computer system for generating a dynamic image of tissues for display on said display, said generating for displaying on said display the tissues realistically representing corresponding actual biological tissues of a particular patient; a user tool generator including specialized software executing on a computer system for generating a tool model of a user tool for dynamically interacting with said dynamic image of tissues via manipulations provided by a user input for display on said display; and a user interface to the computer system configured for permitting a user to adjust the dynamic image of tissues displayed on said display by adding or modifying features of said tissues to aid a surgical operation. The modeling system is configured for use in an operating room during the medical procedure on the particular patient.

Further provided is modeling system for performing a surgical procedure, comprising: a touchscreen display; a database for storing a library of a plurality of models of different organs and/or tissues, wherein said database is also configured for storing medical images of a particular patient, wherein said modeling system is configured for building a case to support said surgical procedure in advance of said procedure by creating models for the particular patient using the patient medical images; a user interface for selecting said case from a plurality of such cases for loading in said modeling system; an image generator including specialized software executing on a computer system for generating a dynamic image of tissues for display on said display based on said selected case, said generating for displaying on said display the tissues realistically representing corresponding actual biological tissues of the particular patient; a user tool generator including specialized software executing on a computer system for generating a tool model of a user tool for dynamically interacting with said dynamic image of tissues via manipulations provided by a user input for display on said display; a user interface to the computer system configured for receiving inputs from the user for configuring the modeling system via said touchscreen display; and an interface to connect to an interface of an external surgical system or tool present in the operating room for receiving data from the external surgical system or tool for use in generating said dynamic image of tissues for display consistent with an operation of the external surgical system or tool.

The above modeling system can be configured for use in an operating room during a surgery on the particular patient.

Also provided is a method of using a modeling system (such as described herein) to support a medical procedure, comprising the steps of:

provide a computer system configured for use in an operating room;

providing a display connected to said computer system;

obtaining patient image information about the biological tissues of a particular patient for storing in said computer system;

generating, using specialized software executing on the computer system, a dynamic image of the biological tissues of the particular patient for display on said display, said generating utilizing said patient image information such that said dynamic image of tissues is displayed on said display realistically representing corresponding actual tissues of the particular patient;

generating, using said computer system, a user tool model for dynamically interacting with said dynamic image of tissues via manipulations input by a user for display on said display;

adjusting, using a user input to said computer system, the dynamic image of tissues displayed on said display by adding or modifying features of said tissues for display to adjust anatomical structures that are in the actual biological tissue of the particular patient; and generating, using the computer system, a realistic simulation of at least a part of the surgical procedure being performed on the particular patient for display on said display showing interactions between the dynamic image of tissues and the user tool model according to inputs by the user.

Still further provided is a method of using a modeling system (such as described herein) to support a medical procedure, comprising the steps of:

providing a computer system configured for use in an operating room;

providing a 3D display connected to said computer system;

obtaining patient image information about the biological tissues of a particular patient;

building a case to support said surgery in advance of said surgery by creating models for the particular patient using the patient medical images configured for generating dynamic images of the biological tissues of the particular patient;

generating, using specialized software executing on the computer system, the dynamic images of the biological tissues of the particular patient for display on said display using said case, said generating utilizing said patient image information such that said dynamic image of tissues is displayed on said display realistically represent corresponding actual tissues of the particular patient;

generating, using said computer system, a user tool model for dynamically interacting with said dynamic image of tissues via manipulations input by a user for display on said display;

adjusting, using a user input to said computer system, the dynamic image of tissues displayed on said display by adding or modifying features of said tissues for display to adjust anatomical structures that are in the actual biological tissue of the particular patient;

generating, using the computer system, a realistic simulation of at least a part of the surgical procedure being performed on the particular patient for display on said display showing interactions between the dynamic image of tissues and the user tool model according to inputs by the user;

receiving data from an external surgical system being used during the surgery, said data being used by said simulation tool to ensure that said dynamic image of the biological tissues is consistent with an operation of the external surgical system; and providing a capability of warning the user about proximity of one or more surgical tools to a specific anatomical structure of the patient.

Also provided are additional example embodiments, some, but not all of which, are described hereinbelow in more detail

BRIEF DESCRIPTION OF THE DRAWINGS

The patent or application file contains at least one drawing executed in color. Copies of this patent or patent application publication with color drawing(s) will be provided by the Office upon request and payment of the necessary fee. The features and advantages of the examples of the present invention described herein will become apparent to those skilled in the art to which the present invention relates upon reading the following description, with reference to the accompanying drawings, in which:

FIGS. 2-11 and 12-18 are screen shots of example display and/or control interfaces for the example SNAP tool.

DETAILED DESCRIPTION OF THE EXAMPLE EMBODIMENTS

Figure 1:
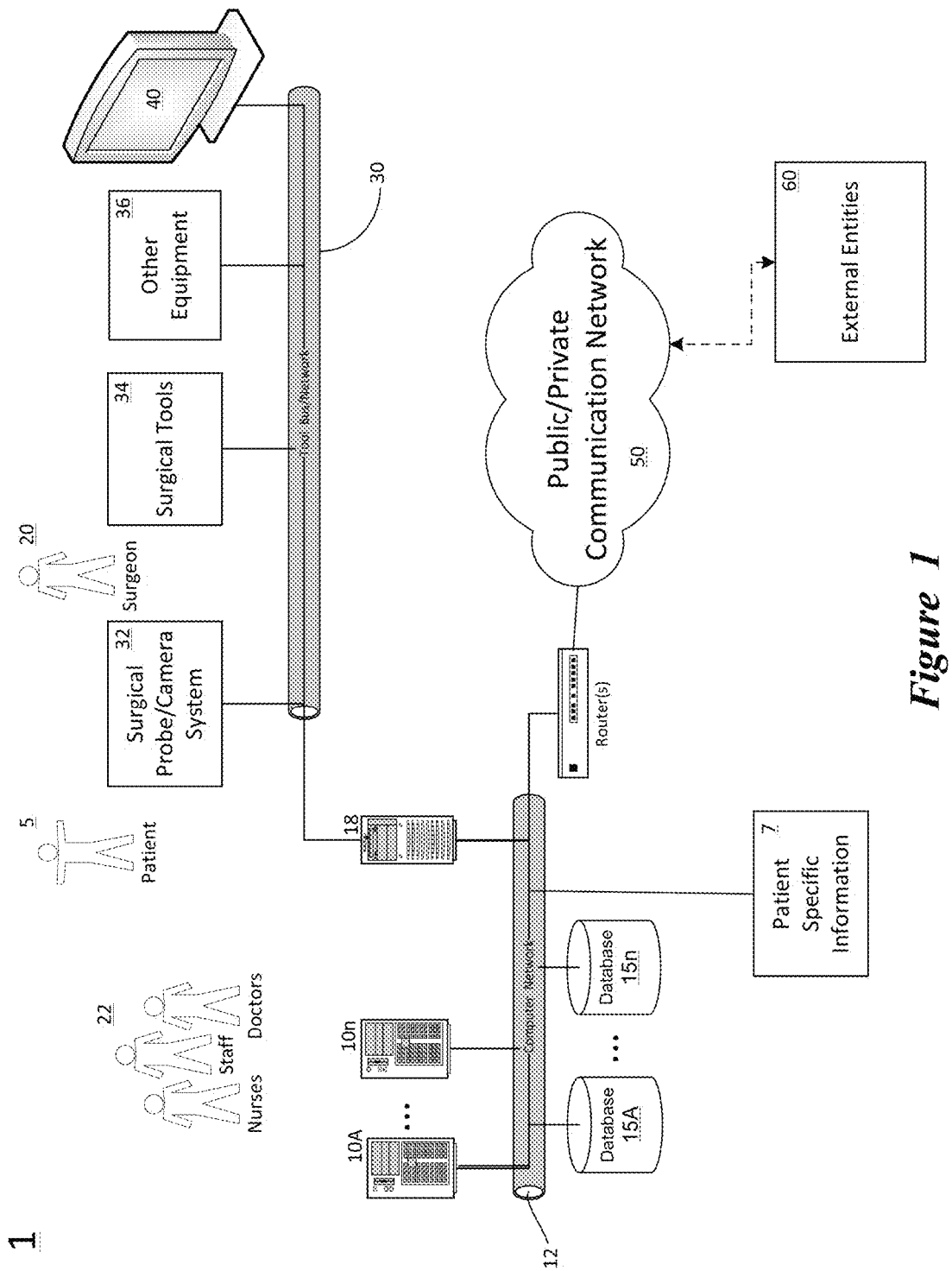
FIG. 1 is a block diagram showing an example system structure and interfaces for utilizing the SNAP surgical tool(s) disclosed herein.

The terminology used herein is for the purpose of describing example embodiments only and is not intended to be limiting. As used herein, the singular forms "a", "an" and "the" are intended to include the plural forms as well, unless the context clearly indicates otherwise. It will be further understood that the terms "comprises" and/or "comprising," "including," "having," "containing," when used in this specification, specify the presence of stated features, integers, steps, operations, elements, and/or components, but do not preclude the presence or addition of one or more other features, integers, steps, operations, elements, components, and/or groups thereof.

This application incorporates all of the teachings of U.S. patent application Ser. No. 14/008,917 filed on Sep. 30, 2013, and PCT application Serial No. PCT/US13/42654 filed on May 24, 2013, which provide design information to be utilized for the improvements discussed herein.

The disclosed example surgical graphical tool (SNAP) integrates with operating room technology to provide advanced 3D capabilities and augmented reality, allowing surgeons to enhance their surgery performance and prepare in advance. The SNAP tool provides neurosurgeons unique virtual-reality guidance to determine the safest and most efficient pathway to remove cerebral tumors and treat vascular anomalies, for example, among other uses.

The SNAP imports the 3D planning of craniotomy, head position, path approaches to the pathology, for example for Keyhole and other minimally invasive techniques. The SNAP allow the surgeon to see in advance the expected surgeon eye view.

With the SNAP tool, surgeons can execute their surgery plan while in the operating room utilizing a particular patient's actual CT/MRI (and other) scans, allowing enhanced accuracy and efficiency. SNAP also provides innovative features that allow surgeons to see behind arteries and other critical structures, in a rotatable 3D format that can be modified to make the images more useful to the surgeon. For example, SNAP provides the ability to rotate images or make the semi-transparent, to aid the surgeon in visualizing the operation. SNAP makes use of advanced imaging technology that allows a surgeon to perform a real-life "fly through" of a "patient-specific" surgery. The tool provides preparation support outside the operating room and can also be utilized to take the pre-planned pathway into the operating room itself to be used by the surgeon (and his staff) during a procedure.

The SNAP obtains the tracing coordinates of surgery tools, navigation probe, microscope focal point etc. by either connecting to OR intra-operative tracing navigation systems. The SNAP provides 3D navigation model that slows enhanced situational awareness. SNAP can receive image or tracking/navigation information from any of these surgery tools that are configured to collect such information, and such information can be used by the SNAP system to cause the high-resolution image displayed to the surgeon to correspond to the received information. For example, the SNAP image might track the location of the tool in the displayed image, or update the image based on visual information provided by the tool, for example.

SNAP proximity warning systems operates in a similar way that Ground Proximity Warning System (GPWS) and An Airborne Collision Avoidance System (ACAS), Terrain Collision Avoidance System (TCAS) and other similar systems in airplanes which indicate and warns the air crew from proximity and/maneuver that may cause a proximity to the ground and other obstacles. SNAP proximity warning systems operates includes the following main stages:

The SNAP proximity warning systems can automatically mark anatomical structure that the surgeons need to avoid. Such anatomical structure may include fiber track, nerves, vessels, arteries etc.

The SNAP proximity warning systems allows a manual placement of markers within the 3D or 2D navigation scene. Those markers can either mark obstacles and anatomical structure to avoid or mark a Target that surgeon will navigate to. Every marker that is being placed can be labeled, have a specific color, specific shape etc.

The indication of the warning of the SNAP proximity warning systems can be visual (for example changes in color), vocal (sound) and others.

The SNAP can allow creating a Trajectory. By marking an Entry point and then associating this entry point with the above marker/target, the SNAP creates a Trajectory that allows to navigate from the Entry point to the Target.

The SNAP Path planner allows to connect several, Markers, Target and Entry points and do create Path. Multiple Paths can be created. Path can be a desired route to follow or a Path to avoid.

Similar to airplanes Instrument Landing System (ILS), the SNAP provides visual graphic guidance to the surgeon. As far as the surgeon maintains his movements within the guided markers, he will get accurately from point A to point B (from Entry point to Target).

The tool provides institutions (e.g., hospitals) and their respective surgeons with the opportunity to reduce surgical errors, decrease the amount of surgical waste and related costs, reduce operating room time, and minimize the high-risk nature of the procedures. The tool provides for an opportunity to maintain high quality in neurosurgery training, and for taking the Education outside of the operating room: Halstedian training for surgery skills depends on a large volume, a wide variety of cases, and almost endless resident's time in the hospital. Recent developments have forced a rethinking of the Halstedian system. The recent constellation of pressures on Halstedian system includes; restricted work hours, increased public scrutiny, and reduction in operative experience.

Rehearsal using the tool can reduce the need for follow-up procedures and adjustments. For example, the tool, when used for aneurism surgery, using the tool can reduce the need for adjusting or replacing an aneurism clip. Adjustments and replacement of the clip can typically result in extended temporary occlusion and overall longer procedure time. This may increase overall procedure risk.

As will be appreciated by one of skill in the art, the example embodiments disclosed herein may be actualized as, or may generally utilize, a method, system, computer program product, or a combination of the foregoing. Accordingly, any of the embodiments may take the form of an entirely hardware embodiment, an entirely software embodiment (including firmware, resident software, microcode, etc.) for execution on hardware, or an embodiment combining software and hardware aspects that may generally be referred to herein as a "system." Furthermore, any of the embodiments may take the form of a computer program product on a computer-usable storage medium having computer-usable program code embodied in the medium.

For example, the features disclosed herein can be implemented using a networked computer system 1 provided in a hospital setting (such as in an operating room), as shown in FIG. 1. This system can be provided in the surgical setting, where a surgeon 20 operates on a patient 5 supported by various surgical staff 22. Such a system 1 integrates one or more servers (e.g., PCs) 10A-10$n$ accessing data from one or more databases 15A-15$n$ that are networked together using a computer network 12. The system will execute proprietary software provided to implement the functions and other features described herein. One or more computers 20 can be used to interface with various surgical tools such as a surgical probe/camera 32, other surgical tools 34, and/or other equipment 36 connected to the computer(s) 20 using one or more computer busses or networks 30 as an interface between the computer 18 and the tools. Note that in some situations, all of the computers 18, servers 10, and databases 15 might be housed in a single server platform.

The system is connected to a high-resolution 3D display 40 on which the surgeon can monitor the operation and activity of the various tools 32, 34, and 36. In some cases, a display may not have 3D capability.

The system is configured with patient specific parameters 7 which include imaging details of the patient including images prepare from the patient's available CT and MRI images that were previously obtained, and other information that concerns the simulated models such as patient age, gender, and so on (some or all of which may be obtained from external entities, such as medical databases, laboratories, or other sources, for example). The system utilizes tissue information parameters obtained from a system database(s) that describe tissue and organ features. The system can be configured to interact with one or more external entities 60 via a communication network 50, such as the Internet, where desired.

Any suitable computer usable (computer readable) medium may be utilized for storing the software for execution on one or more of the computers for realizing the disclosed processes and for storing the disclosed data and information. The computer usable or computer readable medium may be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires; a tangible medium such as a portable computer diskette, a hard disk, a random access memory (RAM), a read-only memory (ROM), an erasable programmable read-only memory (EPROM or Flash memory), a compact disc read-only memory (CDROM), or other tangible optical or magnetic storage device; or transmission media such as those supporting the Internet or an intranet. Note that the computer usable or computer readable medium could even include another medium from which the program can be electronically captured, via, for instance, optical or magnetic scanning for example, then compiled, interpreted, or otherwise processed in a suitable manner, if necessary, and then stored in a computer memory of any acceptable type.

In the context of this document, a computer usable or computer readable medium may be any medium that can contain, store, communicate, propagate, or transport the program for use by, or in connection with, the instruction execution system, platform, apparatus, or device, which can include any suitable computer (or computer system) including one or more programmable or dedicated processor/controller(s). The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, radio frequency (RF) or other means.

Computer program code for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, Object Pascal, or the like, artificial intelligence languages such as Prolog, a real-time embedded language such as Ada, or even more direct or simplified programming using ladder logic, an Assembler language, or directly programming using an appropriate machine language.

The computer program instructions may be stored or otherwise loaded in a computer-readable memory that can direct a computing device or system (such as described by example system 1 of FIG. 1), or other programmable data processing apparatus, to function in a particular manner, such that the instructions stored in the computer readable memory produce an article of manufacture including instruction means which implement the functions/acts specified herein.

The software comprises specialized computer program instructions that are executed by being provided to an executing device or component, which can include a processor of a general purpose computer, a special purpose computer or controller, or other programmable data processing apparatus or component, customized ad described herein such that the instructions of the specialized computer program, when executed, create means for implementing the functions/acts specified herein. Hence, the computer program instructions of the customized software are used to cause a series of operations to be performed on the executing device or component, or other programmable apparatus to produce a computer implemented process such that the instructions which execute on the computer or other programmable apparatus the steps for implementing the functions/acts specified in this disclosure. These steps or acts may be combined with operator or human implemented steps or acts and steps or acts provided by other components or apparatuses in order to carry out any number of example embodiments of the invention. The customized software may also utilized various commercially available software such as computer operating systems, database platforms (e.g. MySQL), or other COTS software, as desired.

For an example system, called the "Surgical Navigation Advanced Platform" (SNAP), medical images of an actual patient are transformed into a dynamic, interactive 3D scene. This dynamic and interactive image/model creates a new novel and original standard for medical imagery and has many applications.

The SNAP provides surgeons (neurosurgeons etc.) unique virtual-reality guidance to determine the safest and most efficient pathway to remove tumors (cerebral etc.) and treat anomalies as vascular anomalies for example. The "Surgical Navigation Advanced Platform" (SNAP) can be used as a stand-alone system or an application of surgery navigation systems or used with a 3rd party navigation system for the type of procedures for which the 3rd party navigation system is used. These Procedures include but are not limited to Cerebral, Spine, and Ear, Nose Throat (ENT).

The SNAP allows surgeons to analyze and plan a specific patient's case before surgery, and then take that plan into the operating room (OR) and use it in conjunction with the navigation system during surgery. The SNAP then presents the navigation data into the advanced inter-active, high quality 3D image, with multiple points of view.

The SNAP is actually image guided surgery systems including a medical imaging device that present real time and dynamic multiple line of sights views (from different/multiple perspectives) of the surgery procedure. The image includes the scanned medical image (based on scan such as CT, MRI, Ultrasound, X-ray etc.) and the surgery instruments. It may also include real time video and models based on video form microscope or other sources. The SNAP provides a real time 3D interactive guided image for the surgeon. The orientation of the anatomical structures (i.e. head, brain, knee, shoulder etc.) is marked and pre-registered both in the physical/patient's and the scanned medical image (CT, MRI, Ultrasound, X-ray etc.); therefore, the orientation of the scanned medical image and the real anatomical structures of the patient's under the surgery are synchronized and aligned.

Furthermore, the above pre-registered markers provides a spherical reference for tracking the surgery instruments and the OR microscope (and/or the surgeon head) and therefore allowing to present the surgery instruments image/model in space in relation to the scanned medical image.

The patient's anatomical structures in 2D or 3D and the position and orientation of the surgery instruments are synchronized in real time and are presented to the surgeon with a real time location and orientation of the instruments and markers in space in relation to the anatomical structures.

The SNAP system is capable of preparing cases that have multiple scanned datasets. The built-in "Fusion" mode allows the user to select one dataset to serve as the primary dataset, and add secondary datasets, that will be aligned ("Fused") to the primary scan dataset.

The SNAP system has a unique clip features. The ANY plane IG cube clipping is a feature that the user can "clip" the 3D model from any desired angle, essentially cutting into the model and removing a section to expose the internals of the model. The clipping plane is the plane by which the 3D model is "Clipped" the plane defined by 2 variables—Plane normal (vector) and plane position (The point in space that the plane goes through).

Furthermore, the SNAP system knows to slave the ANY plane IG cube clipping to 3D moving elements in the scene. Since the cube-clipping plane is defined by a normal and a position, we can use moving elements in the scene to define this for the user. The elements are: The navigation probe, the 3D controller (Omni), the corridor, the IG point of view (Eye camera) etc.

Another feature is the Transfer Function. The SNAP system has a special ability to display "Tissue specific intensity". The original dataset slices are collected and stacked to reconstruct a cube of pixels, or what we call the voxels cube. The 3D model is a cube volume of voxels. The transfer function is used to map each voxel intensity value to color and opacity. That way we control the tissue intensity and enabling a surgeon to see what he typically can't see. This innovative feature allows surgeons to see behind arteries and other critical structures, something not possible until now.

The SNAP can present models on one or multiply windows on the same screen or on multiply screens. Examples for the features and applications of the SNAP, multiple features can be activated side by side on the screen.

A typical system configuration is comprised of the following main components: (1) System mounted cart for mobility; (2) Medical grade isolation transformer; (3) a Personal Computer (or server) running Microsoft Windows 7 operating system; (4) a high end nVIDIA graphics adapter for high quality graphics; (5) a 27" or 32" full HD touch screen display; (6) a medical grade keyboard and mouse; and (7) a SNAP Software Application for implementing the features described herein. Such a system is shown by the block diagram of FIG. 1A, where an example mobile cart mounted SNAP system 70 comprising a touchscreen monitor 71 is configured with a PC 72 and a power system 73, all of which can be provided in the operating room. The example system 70 is connected to a navigation system 75 provided in the operating room, such as the example Image Guided Surgery (IGS) System, from which the SNAP system 70 can receive data so that the SNAP system 70 can display high resolution, realistic 3D images that follow the operation of the navigation system, effectively enhancing the operation and display capabilities of the navigation system with the SNAP high-resolution imaging capability based on the images of the specific patient being operated on.

Figure 1A:
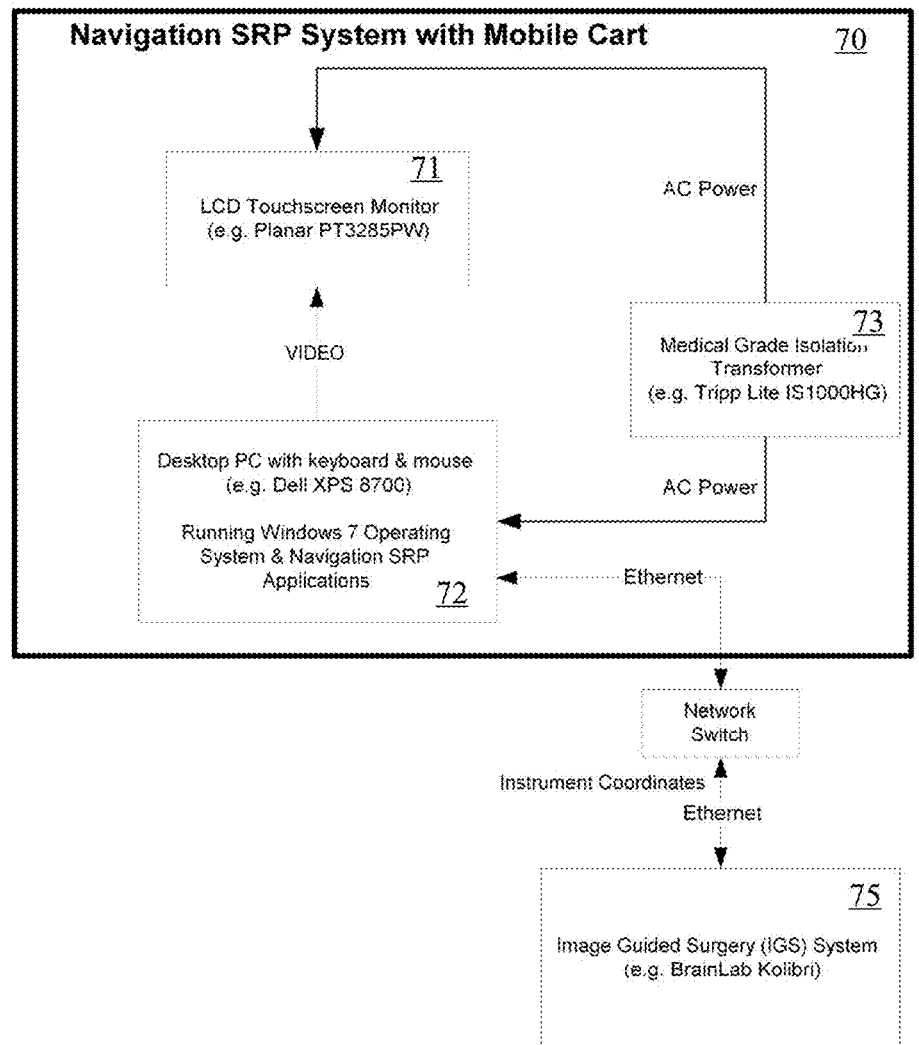
FIG. 1A is a block diagram showing example SNAP tool components for a mobile cart embodiment.
Figure 1B:
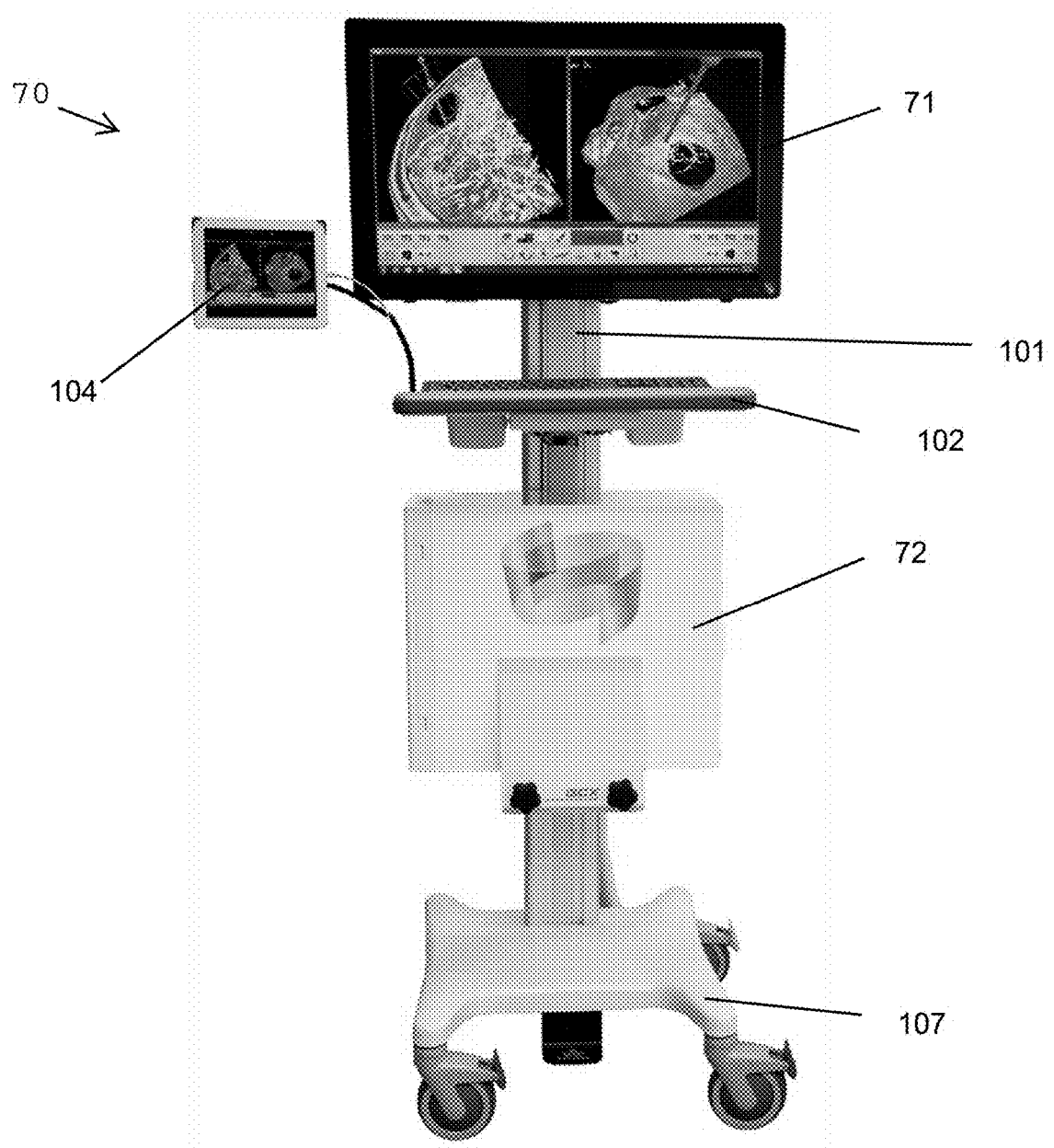
FIG. 1B is a graphical representation of example SNAP tool components for the mobile cart embodiment.

An example cart mounted portion of the system 70 of FIG. 1A is shown in FIG. 1B, showing a main high-resolution display 71 with supplemental display 104, mounted on a stand 101 with a keyboard 102, computer 72, and mobile platform 107, all configured for use in an operating room environment. The power system and the navigation system are not shown in this Figure. If necessary, this configuration can be networked to one or more additional servers using an Ethernet network, for example.

The Surgical Navigation Advanced Platform (SNAP) is intended for use as a software interface and image segmentation system for the transfer of imaging information from CT or MR medical scanner to an output file. A tissue segmentation window is provided to edit and update tissues segmentation to prepare a case. The change in tissue segmentation is reflected in the 3D image, and the result can be saved as part of the case file. It is also intended as both pre and intra-operative software for simulating/evaluating surgical treatment options. The Surgical Navigation Advanced Platform (SNAP) is a pre and intra-operative tool to simulate/evaluate surgical treatment options.

The system will typically provide EMC immunity that can be adapted for an operating room, and will utilize touchscreen operation for navigation, typing, and image manipulation. The system can store individual patient cases using a case file, which can be loaded into the system as desired. A surgeon can create a case from scratch, using scanned information (e.g., MR, or CT DIACOM image data files) and patient data of a particular patient. These cases can be edited and updated as desired. Editing windows can be used to edit and manipulate the images and files.

Generic models of various organs and tissues can be provided, which can be overlaid with patient specific models based on patient imaging or other diagnostic tools or laboratory inputs. Hence, for organs or other features not of particular interest, the system can use generic models (e.g., eyes or other organs) where patient specific information is not needed for the intended treatment.

The Surgery Navigation Advanced Platform displays patient specific dynamic and interactive 3D models with real time navigation data. When performing a navigation session, the tool can be used to verify the accuracy of the SNAP navigation pointer location (provided on the SNAP high resolution display) by pointing and touching visible structures on the patient (i.e. tip of nose, ear lobes) and verifying that the pointer on the SNAP screen points to the same location in the 3D model.

Figure 1C:
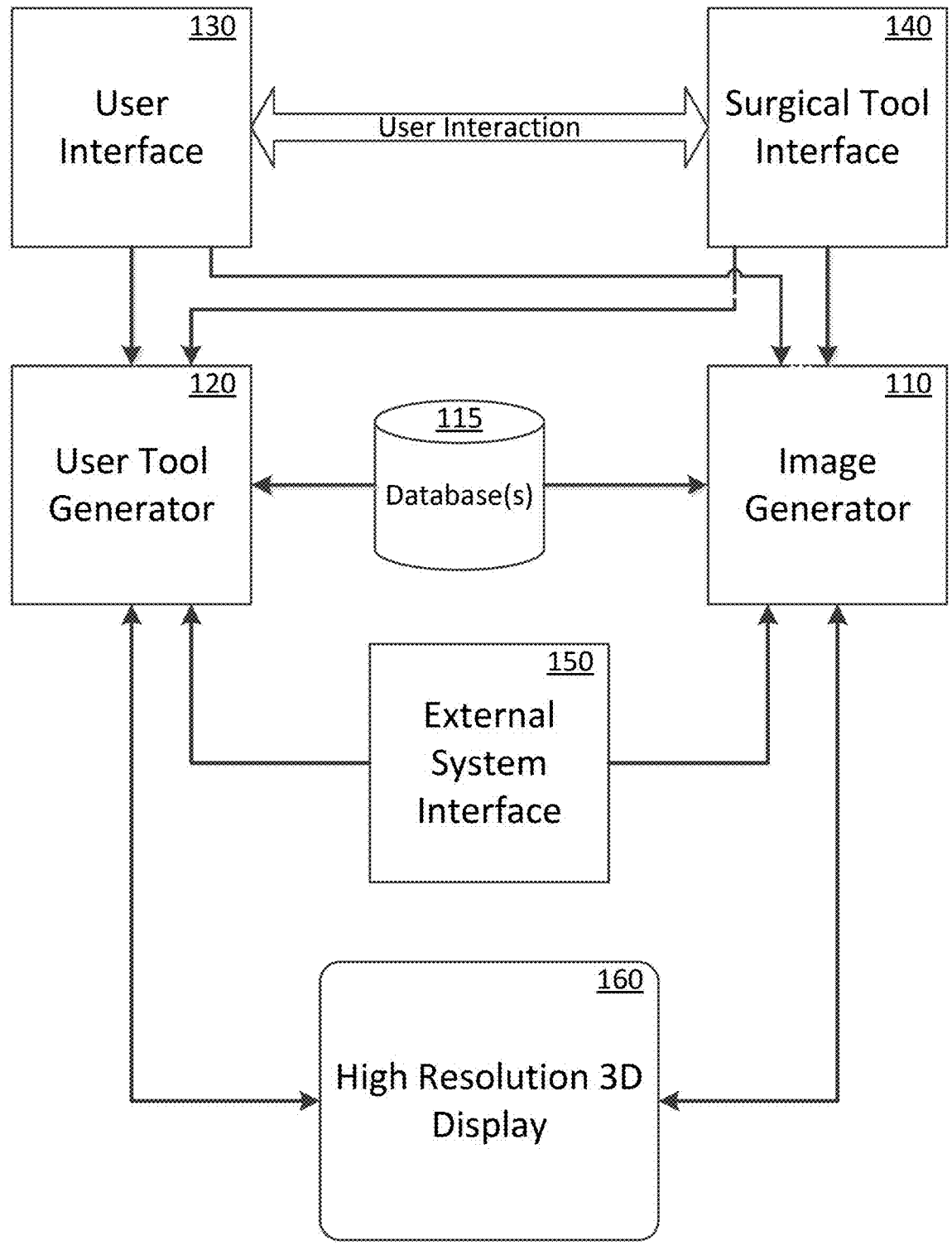
FIG. 1C is a block diagram showing example software interfaces for the example SNAP mobile care embodiment.

FIG. 1C shows an example of the primary processing routines, driven by software modules, which generate the images provided by the SNAP tool. The Image Generator 110 generates the realistic tissue images for display on the display 160, using information stored on the database 115, such as generic tissue images, patient specific images, and the like. The image generator 110 assign visual representation of each segment (shadow texture and so on) and the mechanical Properties and other modeling features will provide the realistic images.

Similarly, the user tool generator will generate realistic images of surgical tools that are displayed dynamically interacting with the tissue images generated by the image generator. In a surgical environment, the tool images displayed on the display 160 may represent actual surgical tool interfaces 140, representations of which could be generated for display by the image generator 110 or the user tool generator 120, for example. The surgical tool interface may dynamically interact with the tissue images generated by the image generator 110. Again, specifications and details about the tool images may be stored in the database 115. Note that because the display 160 may be a touchscreen display, the display 160 may act as the user interface 130, along with other devices such as a keyboard, mouse, or other input device.

The SNAP tool also provides an external system interface 150 that allows the system to interface to other external systems that provide navigation or other functions to the surgeon, so that the SNAP tool can generate images that are consistent with the outputs of the external systems, e.g., mirror the navigation or update the imaging based on the operation of the external system(s). The SNAP tool can then update its display images appropriately for providing an integrated view to the surgeon in high resolution, 3D images that interact with the graphical tools.

Once the surgery tools and the other objects are selected by the surgeon, they are integrated into the virtual surgery scene displayed by the display 160 and turn into an integrated element of the simulated scenario including realistic visual features and mechanical properties and operation properties features that are applied to each one of those selected items, for example—displayed scissors have the real mechanical characteristics and will cut as the real scissors do, and, Aneurysm clips, when placed at the vessel, blocks the blood flow. In this manner, the displayed tools interact with the tissue models in a realistic manner, but in a way that surgeons can manipulate to provide viewpoints not possible in the real world, such as by making various features transparent, rotating images, reversing a procedure, etc.

The interactive image/scene that is displayed to the surgeon is constructed from elements that are both volumetric rendered elements and surface rendered elements. Furthermore, each element, volume or surface, interacts with one or more elements that are volume. Interaction between elements includes, but is not limited to, physical interaction such as: a collision model implemented to represent the interaction between elements that results with movements and/or reshape of elements that replicate the actual physical movements of the element according to physical conditions, such as pressure, elements material (elasticity, stickiness etc.), and collision condition such as collision angels and elements orientation.

The rendering process equation can account for all lighting shadow and shadowing phenomena and produce a final output stream that incorporates all the visual elements.

Anatomical structures that were created using a Tissue Paint or a Magic Tissue Wand algorithm and integrated with the scanned images are an integrated part of the image. For example, a vessel having anatomical structures that originally were partial and incomplete, after applying the Magic Tissue Paint and Tissue Wand algorithm will become complete anatomical structures with structure that is combined from the original scanned image and the newly created structure. Furthermore, a control (check box) allows to select the newly created structure and to switch between on (showing the new created structure) or off (hiding the new created structure). Additionally, an option is provided for selection to render the newly created structure in a volume and or polygon rendering/reconstruction.

A developed algorithm and software tool provides the user an interface to draw any geometric shape or free hand drawing shape in 2- or 3-dimensions (e.g., line, circle, clinic, ball etc.). The region that is included/enclosed/captured within the said geometric shape (2- or 3-dimensions) is defined as a "Marked Region". The user then, has the ability to define and assign any visual characteristics and any mechanical properties to that "marked region".

Visual characteristics; color/transparency/shading—the new created structure either or with the Magic Tissue Paint, Tissue Wand algorithm or the Marked Region can be presented in any selected visual characteristics of color that can be selected from a library of available colors, and a transparency that can be selected on any level from 0 to 100. Furthermore, the characteristics of shading and shadowing of the new created structure can be modified by tuning the characteristics of the virtual light sources. The virtual light sources characteristics includes: spherical location in space, color of the light, strength of the light, the aspect ratio, the geometric shape of the virtual source etc.

Mechanical properties—the new created structure either or with the Tissue Paint, Magic Tissue Wand algorithm or the Marked Region can be assigned with mechanical properties characteristics. That is, that a mechanical model of a specific tissue can be coupled to the new created structure and therefore, the new created structure will inherent such mechanical properties and will react, dynamically and statically according to those mechanical properties. For example, if a "soft tissue" mechanical properties where assigned to a new created structure, it will react according to a soft tissue. For example, when it will be pushed by a virtual surgery instrument, it will squeeze and reshape according to the force applied and the tissue mechanical model. Furthermore, interaction between new crated structures and other new crated structures, interaction between originally scanned structures and new crated structures and between new crated structures and originally scanned structures are seamless. The mechanical properties coefficients of any anatomical structure (stiffness, elasticity etc.) can be tuned by the user to create a tailored made mechanical behavior.

Real Time Tracking and Feedback—a system to track a real surgery instrument during the surgery. The tracking system transfers the surgery instruments location and coordination in space relative to the orientation and location of a real anatomical structure (for example, specific spot on the patient's head). The instruments' location and orientation is then sent to the surgical simulating system. Feedback is provided to the surgeon based on the patient specific simulation and the instruments' location and orientation. One example for such feedback can be; the system generates feedback to the surgeons for the type of tissue he is dissecting and alarming the surgeon in case that he dissects healthy brain tissue instead of a tumor. Additional example is that after that the surgeon applied an implement on the real anatomical structure (for example an aneurysm clip applied on an aneurysm on the real patient), the system allows the surgeon to rotate the simulated image/model that is precisely oriented as the real anatomical structure based on the tracking, and observe and evaluate the location and efficacy of the placed implant.

This tracking and feedback of the real instrument can be accomplished in a number of ways, such as by using a video system to track the location and movement of the instrument and the patient features. Alternatively (or in addition to video tracking) the surgical instrument may be modified to enable tracking, such as by using GPS, accelerometers, magnetic detection, or other location and motion detecting devices and methods. Such modified instruments may communicate with the SNAP tool using WiFi, Bluetooth, MICS, wired USB, RF communication, or other communications methods, for example (e.g., via surgical tool interface 140 in FIG. 1C).

FIG. 2 shows an image of a virtual view 210 correlated with the tip of a surgery instrument 201: this is an example for an augment, as if a virtual camera was attached to the tip of the instrument 201. With this endoscopic prop view 210 the ability to represent what would be seen on the SNAP screen if the tip of the probe had a camera (simulating the probe as a "virtual endoscope") and provide the ability to rehearse, plan, evaluate, and simulate an endoscopic procedure or other procedures. The surgeon can manipulate the image using the touchscreen toolbar 220. And by touching the model on the screen for rotating, zoom in and out; hence, FIG. 1 shows an example of the Virtual camera view.

Figure 3:

A microscope view is a view from the orientation of the surgery microscope or the surgeon's eyes view. FIG. 3 is an example of a side-by-side microscope view 230 and vital structures view 235. This view can be limited to the view through the craniotomy allowing the surgeon to simulate a navigation and approach to the pathology though the limited accesses of the craniotomy. Additionally, a minimally invasive or keyhole approach or endoscopic approach can be simulated and evaluated allowing surgeon to try, evaluate, and decide which approach will provide the best desired outcome (for example maximum tumor extraction) with minimum risk (for example, approach with no risk of hitting vessels on the way to the pathology). Afterword, by loading the plan, the surgeon can drill/create the craniotomy/approach that he decided on with the aid of the SNAP on the patient head and then to actually navigate and perform the surgery with the SNAP through the above selected approach.

Figure 4:
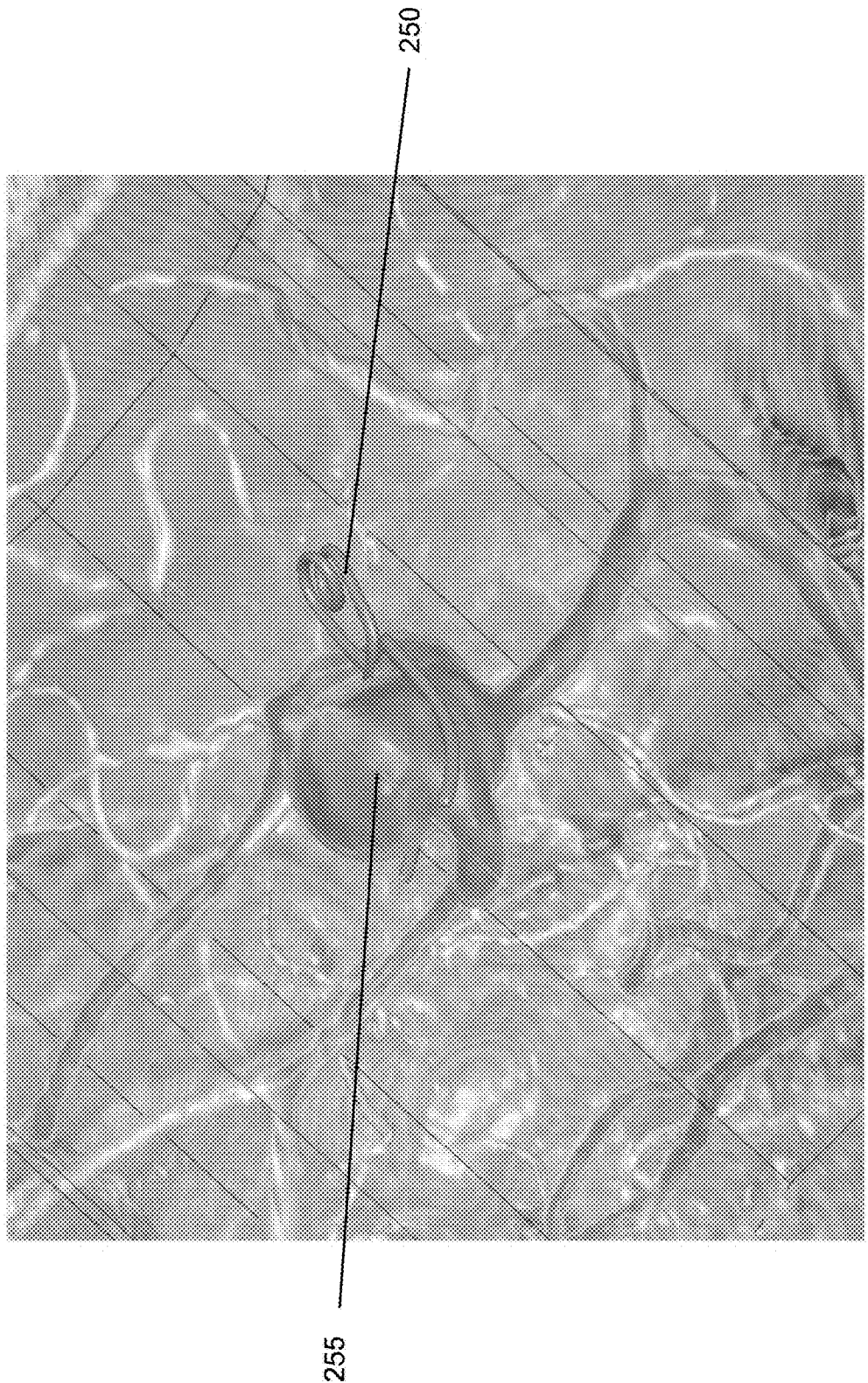

FIG. 4 shows a view from behind the pathology 255 (here an aneurism) that can also be provided, for example a surgeon can "Freeze" the tracking of the pointer/marker or the instrument 250 for investigation the image in the system for further undressing of the orientation of the instrument 250 within the anatomical stature. Freeze pointer in position and manipulate the image (rotate, zoom, change segmentation) so that the surgeon can view from behind the aneurysm to allow seeing if clip 250 is applied correctly, for example.

Figure 5:
Figure 6:

The ability to show multiple points of view provides the ability to view the anatomical image and the model of the surgery instruments surgery simultaneously from multiple viewpoints in real time and you can rotate, shift, zoom each image independently. FIG. 5 shows side-by-side microscope view 260 and sagittal view 265. FIG. 6 shows side-by-side microscope view and coronal view. This allows a surgeon to navigate through the approach that he selected and to see the 3D navigation images of the structures that the surgeon wants to avoid (for example a vessel that is hidden inside or behind a tumor) but cannot be seen in the microscope or the traditional tracking navigation system. The SNAP shows the view that correlates to the microscope view (the surgeon eye view) and additionally to see, in a synchronized manner, the view that the surgeon can not see—the view from behind the pathology.

Figure 7:
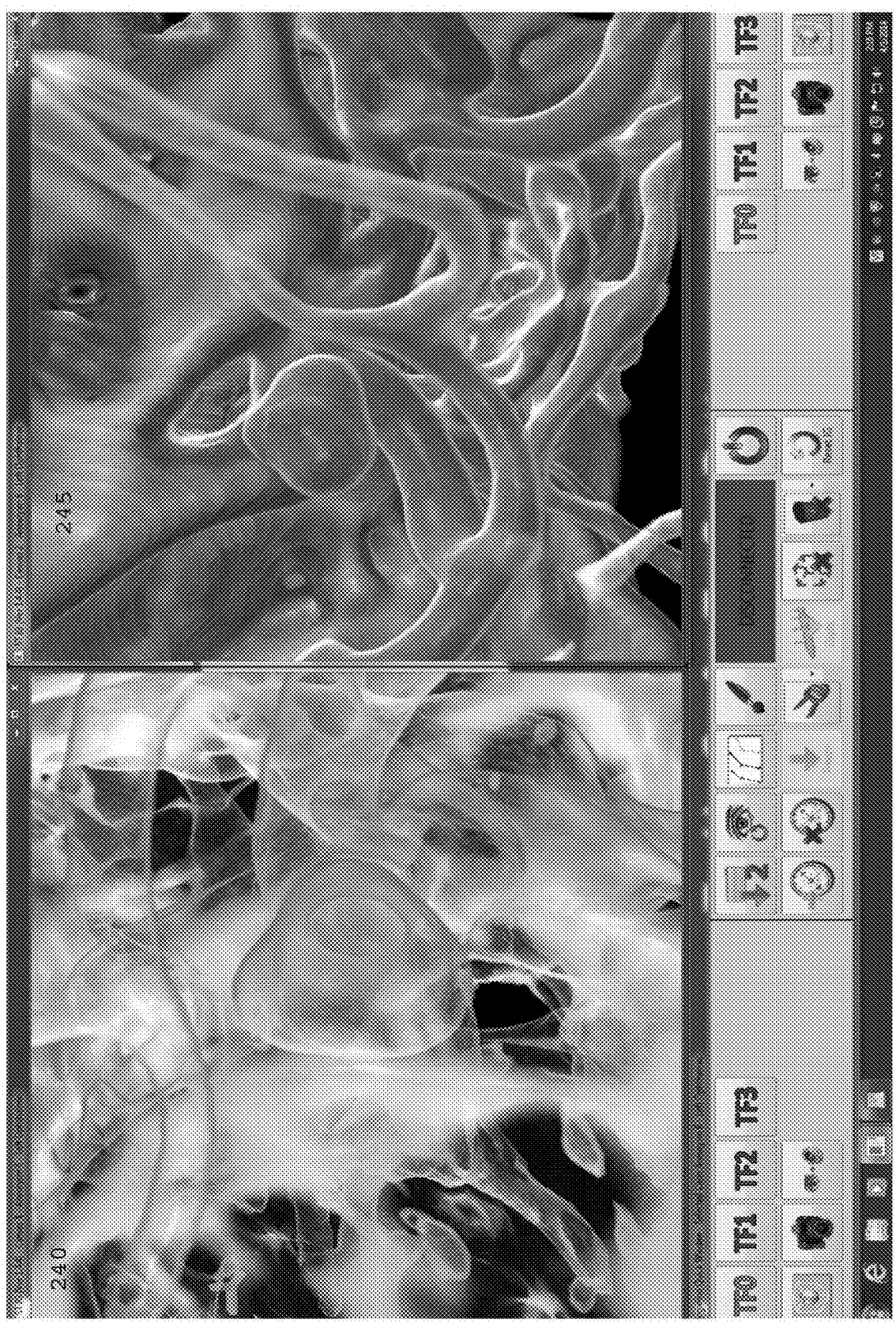

Control segmentation shows each point of view separately; for example, one image can be segmented to show only the vessels while the other image can be segmented to show only the soft tissue. For example, FIG. 7 shows multiple segmentation viewpoints. By manipulating the tissue segmentation we can see clearly the aneurysm neck 240 side by side to a general point of view 245. Independent and simultaneous viewing from different vantage points is provided for enhanced visualization. Independent segmentation can be used for improved visualization of the aneurysm neck and other vital structures.

Figure 8:
Figure 9:
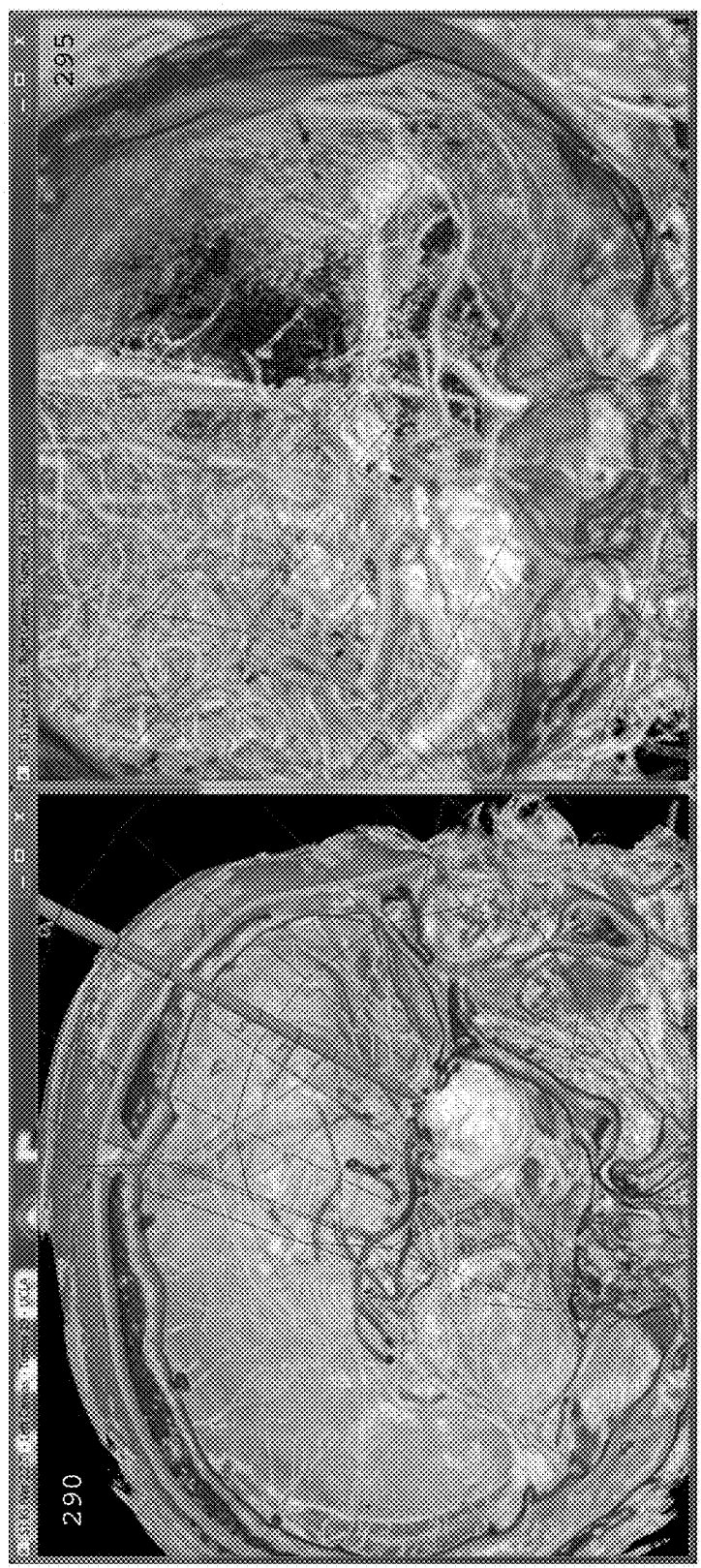

Different modalities (CT and or MRI) can be presented in each image/perspective; for example, one image can be from MRI while the other image can be form CT of the same patients. FIG. 8 shows different segmentation—Side by Side, showing a CTA image 280 and an MRI image 285. Overlaid images can be shown where one image can be combined from multiple modalities; for example MM superimposed/overlaid on CT. FIG. 9 shows an overlay of CT and MM images combined with different segmentations left 290 and right 295. When creating historical case studies, patient specific still images (snapshots) or video files generated during actual surgery or during diagnostic can be stored in the patient case folder. The SNAP software supports all standard Windows bitmap image file formats such as bmp, jpeg, png and gif, and supports all standard Windows video file formats such as mpeg and avi.

Figure 10:
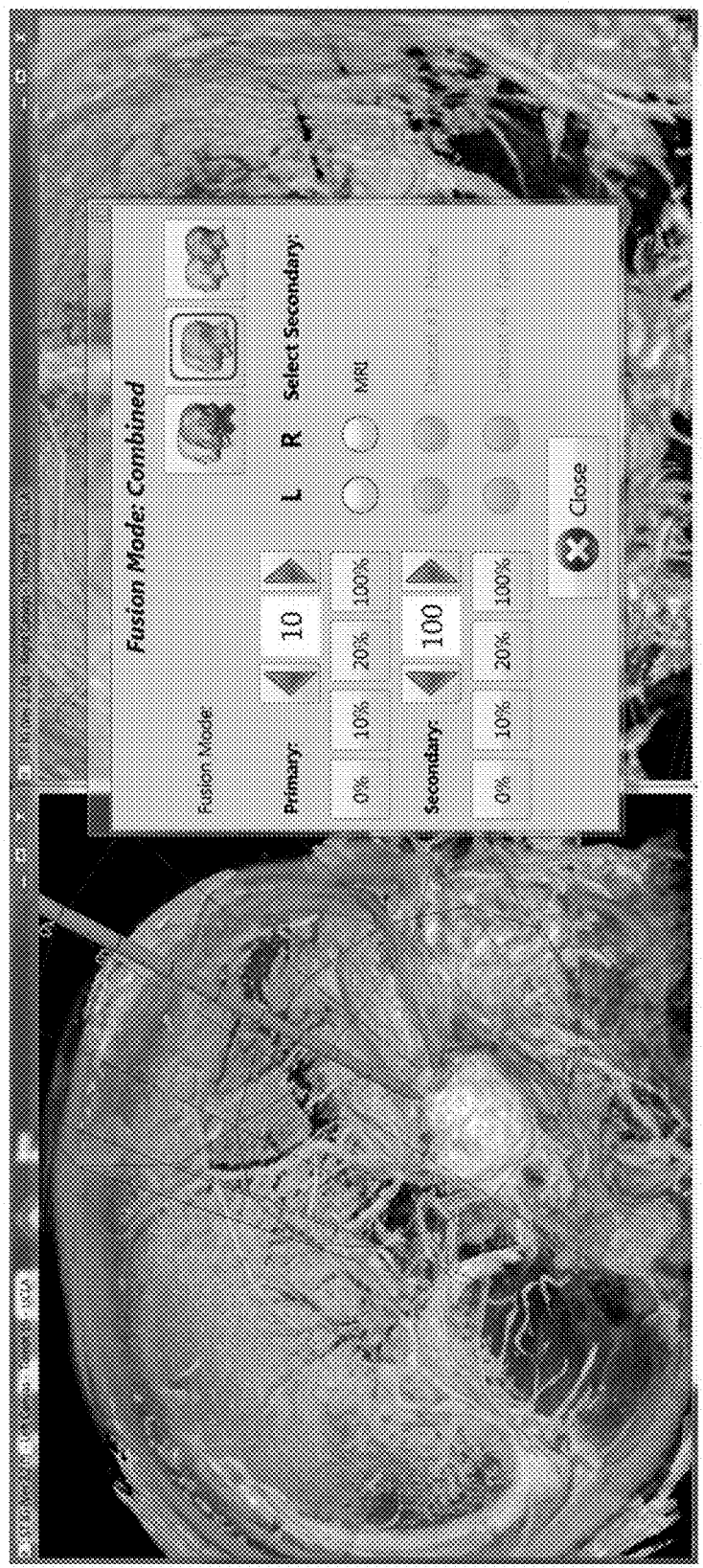
Figure 11:
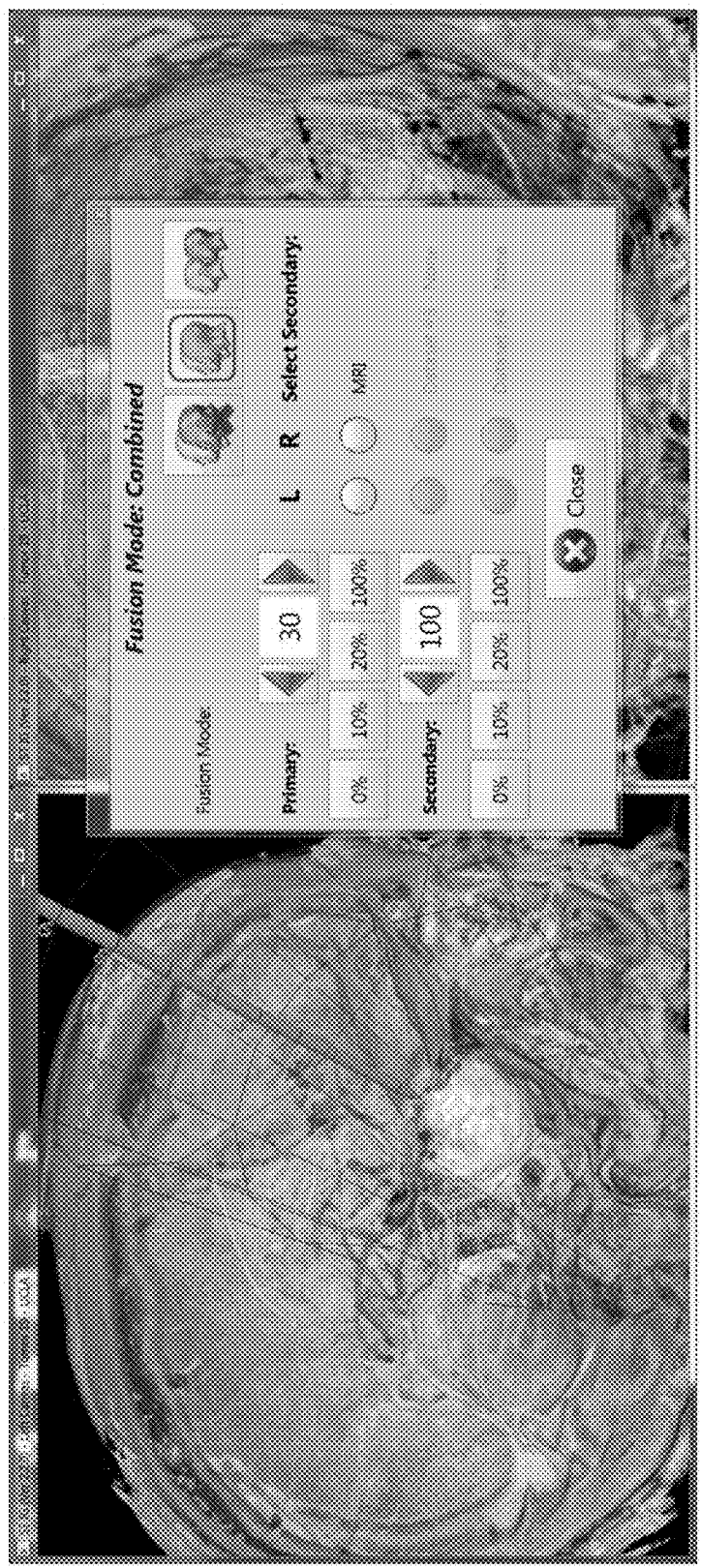
Figure 11A:
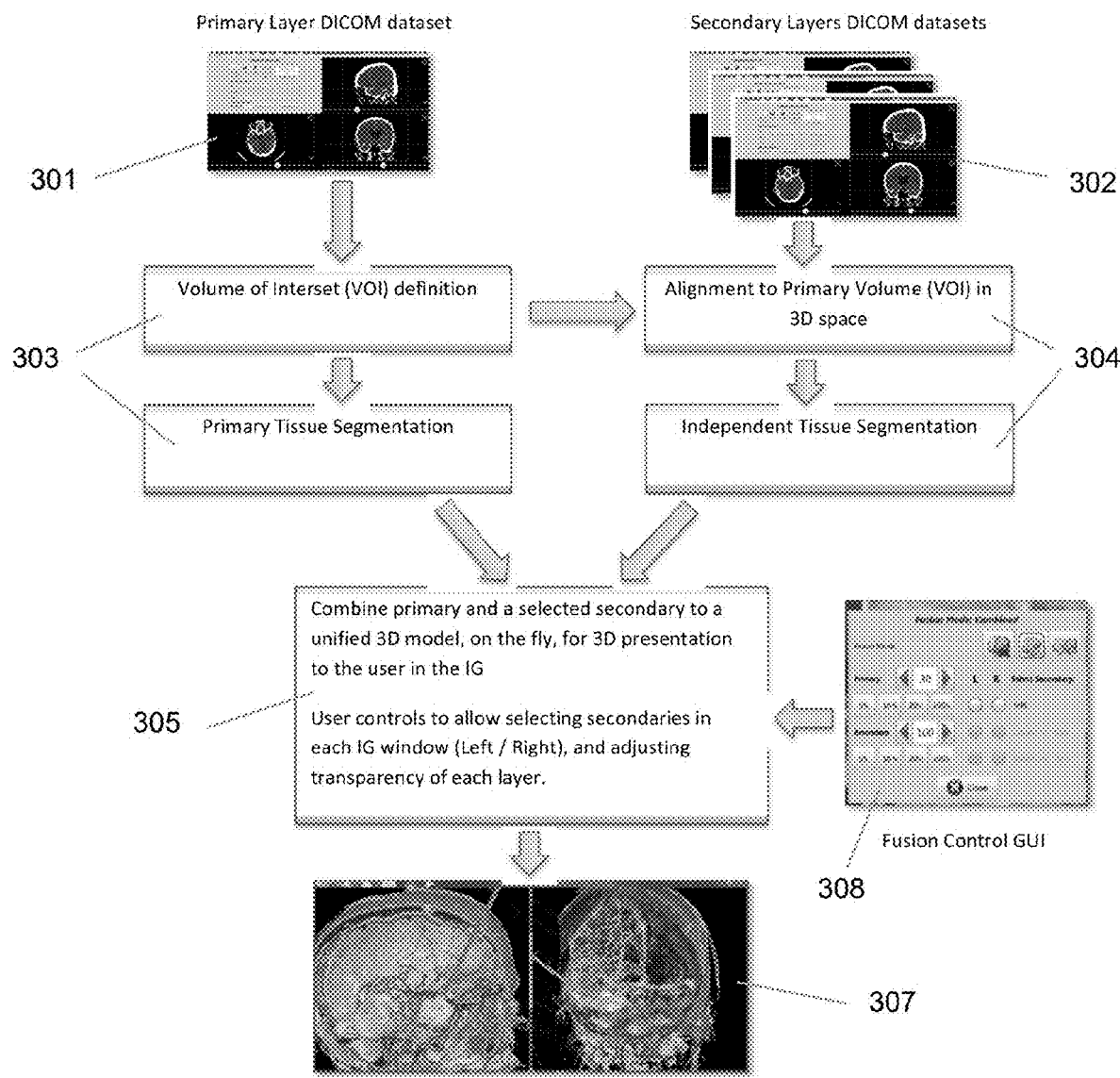
FIG. 11A is a block diagram showing an example fusion processing pipeline method using the SNAP tool for combining differently segmented tissue datasets.

Overlaid images with modalities fade-in/out can also be provided, where in a combined image, one modality can be faded in and out; for example, CT and MM superimposed/overlaid image while the CT is being faded out or overlaid images with segmentation control on each modality; for example, CT and MRI superimposed/overlaid image while the CT is being segmented to show only vessels. FIG. 10 shows an overlay with transparency—CTA at 10% MRI at 100%. FIG. 11 shows an overlay with transparency—CTA at 30% MRI at 100%. FIG. 11A shows an example fusion processing pipeline method using the SNAP tool for taking differently tissue datasets 301, 302 and independently defining and segmenting them 303, 340 for combining them 350 in a manner for presenting the combined image 307 using the transparency specified by the user 308.

Figure 12:
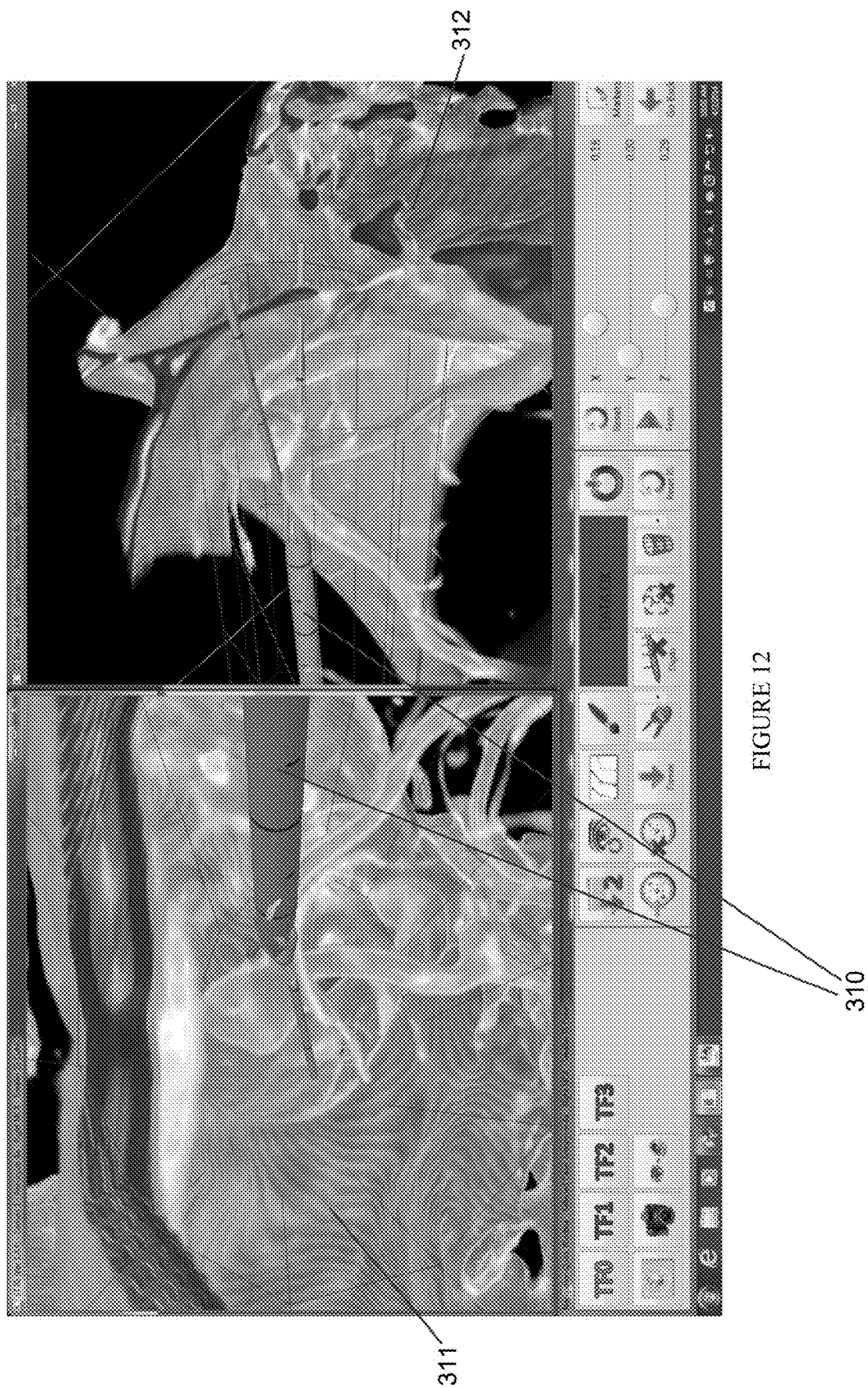

Augmentation proximity and orientation indication allow calculation and generation of indications for proximity of the surgery instrument and or a pointer/marker to a specific anatomical structure. In FIG. 12, for example, a virtual clip 310 is shown at the tip of the navigation probe for evaluation the neck of the aneurysm. The navigation image can be frozen and rotated to examine the clip from multiple points of view, such as a corridor view 311 and a rotated view 312. Markers provided on the virtual clip allows for measuring of the neck and to fit a clip.

Figure 13:
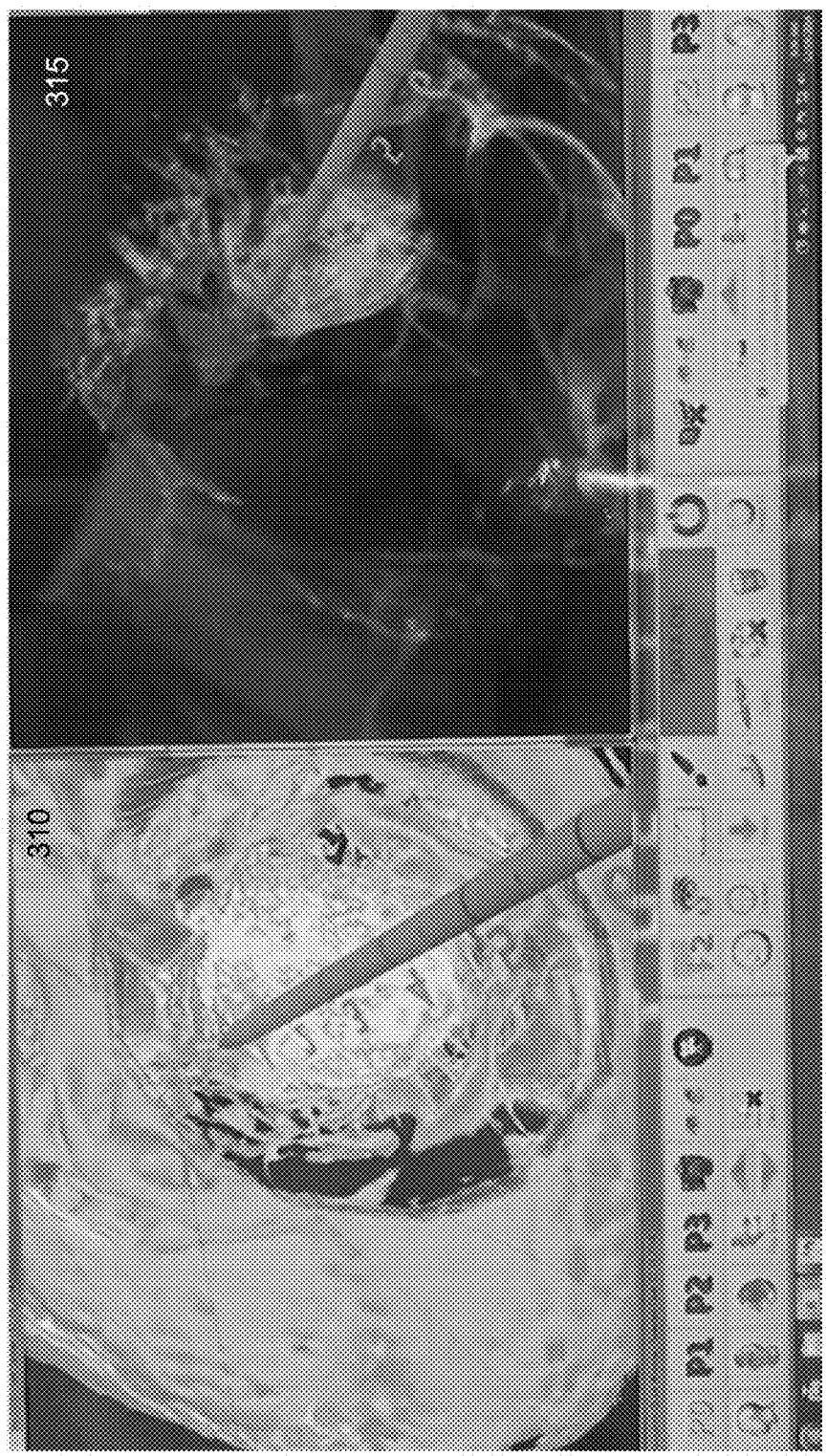

With the SNAP tool, the size of craniotomy is easier to choose, and also allows one to better identify some of the important landmarks. A three-dimensional representation of a tumor gives an excellent view of the tumor boundaries, veins and sinuses to make sure that when the craniotomy is actually started the surgeon can stay away from these structures. FIG. 13 shows a side-by-side craniotomy view 310 and veins view 315.

Figure 14:
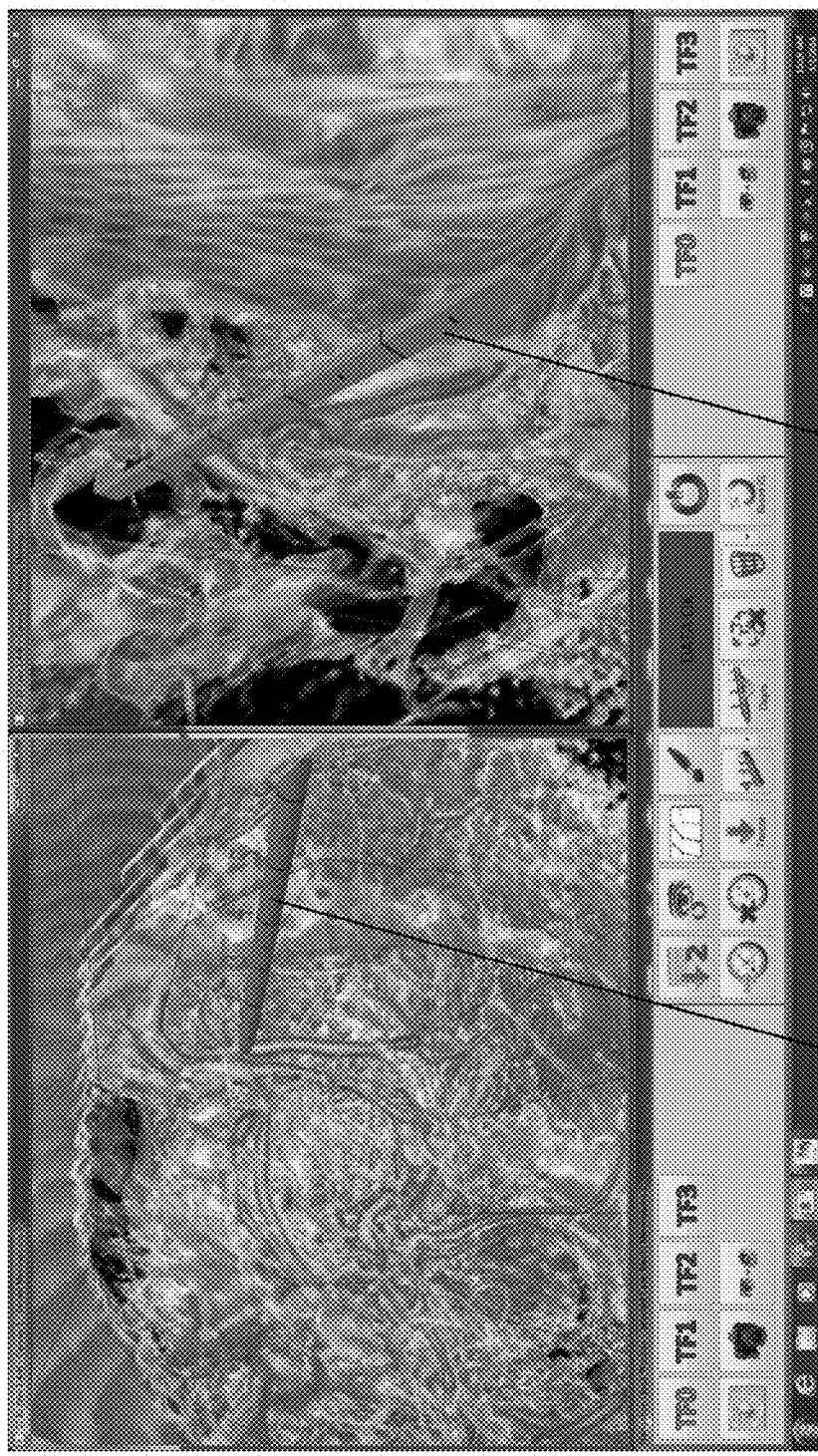
Figure 15:
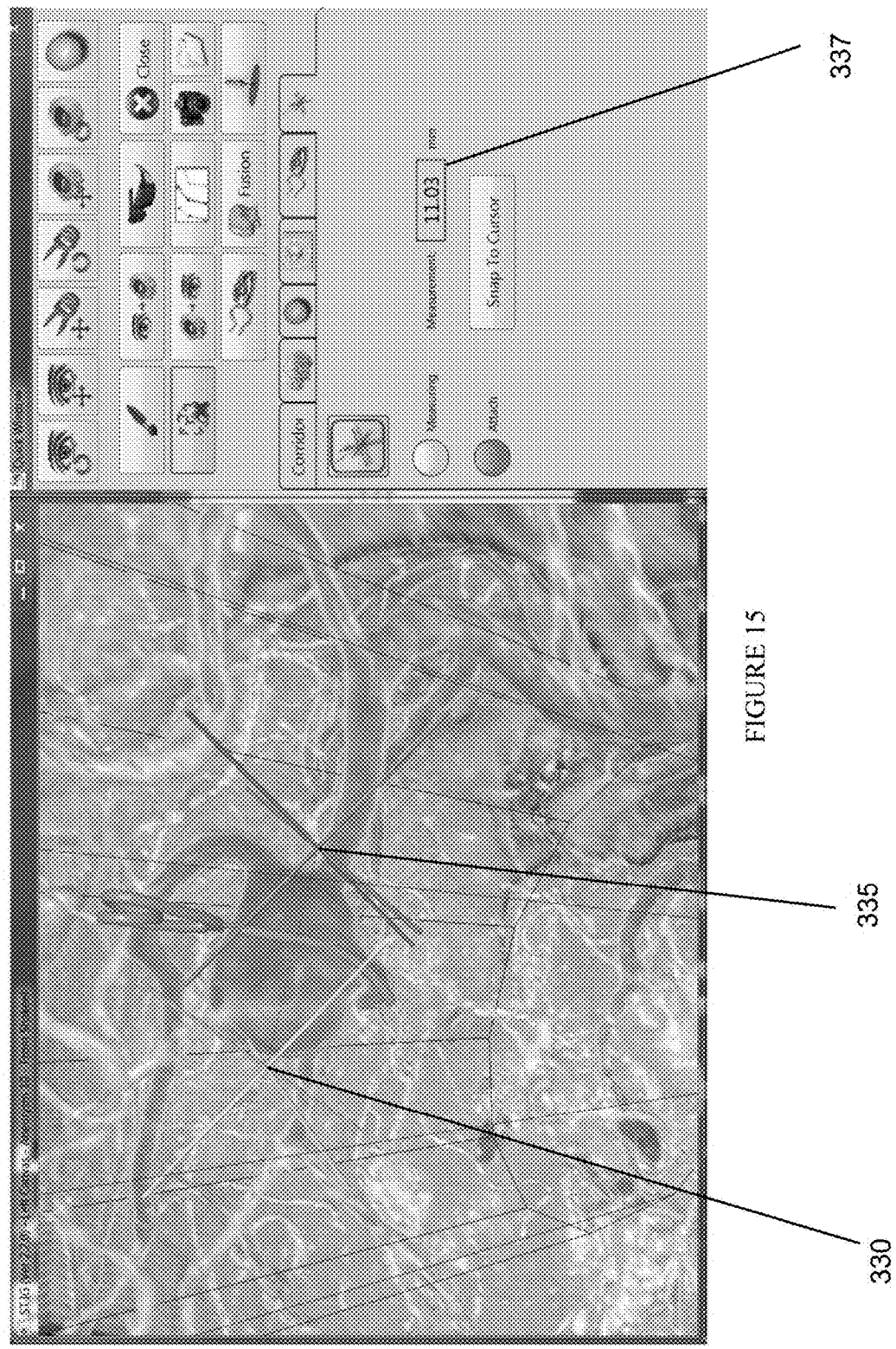

The surgeon can generate a hazard regarding the threshold related to the proximity and orientation indication based on calculation of proximity of the surgery instrument and/or a pointer/mark to a specific anatomical structure. Also, measurement by virtual marking of distance in the marker pointer is supported, for example a virtual side extension to the navigation probe is presented for measuring remaining tumor and distance from arteries. FIG. 14 shows an example of measuring by virtual side extension using the scaled probes 320, 325, while FIG. 15 shows an example of measuring aneurysm size measurement by virtual marking 330, 335 with the resulting measurement shown in the window 337.

Figure 16:
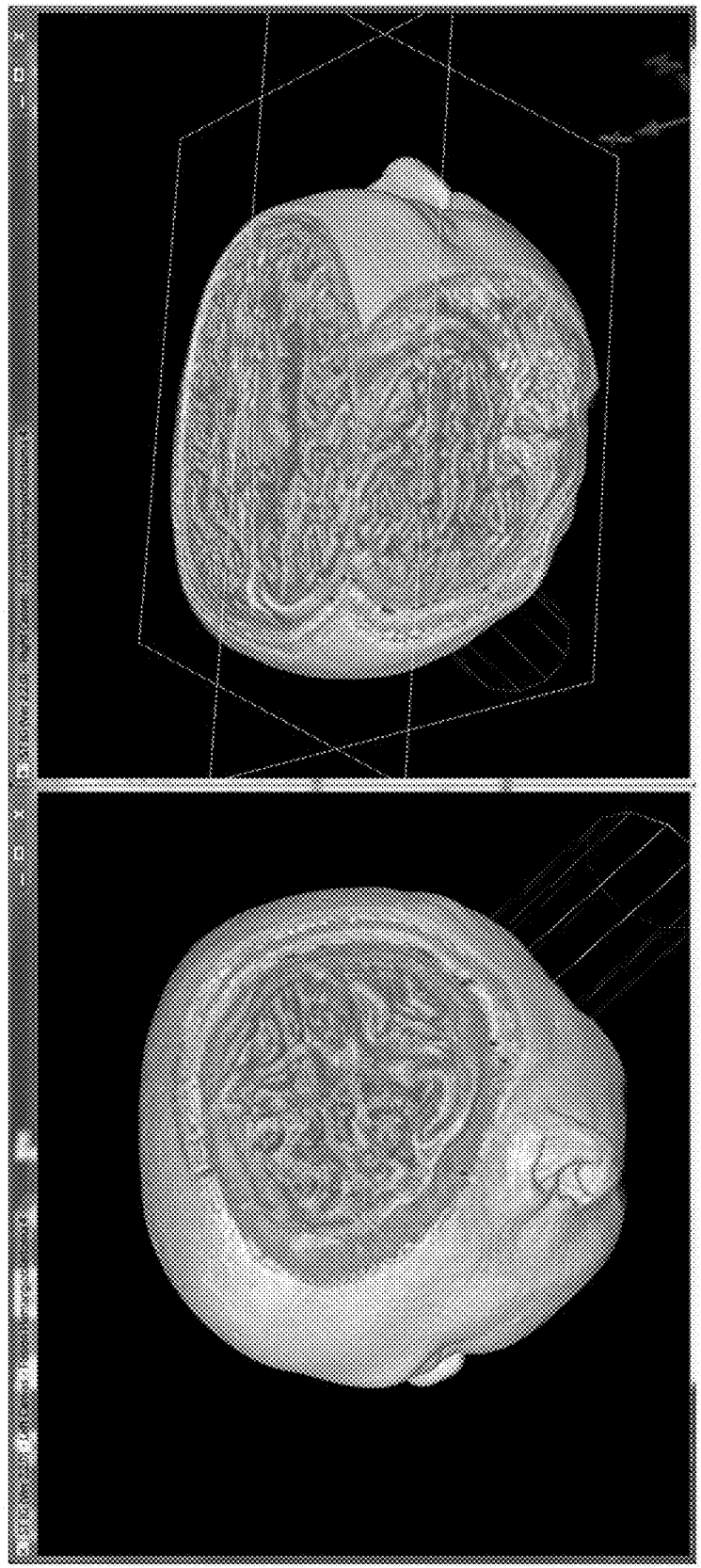
Figure 17:
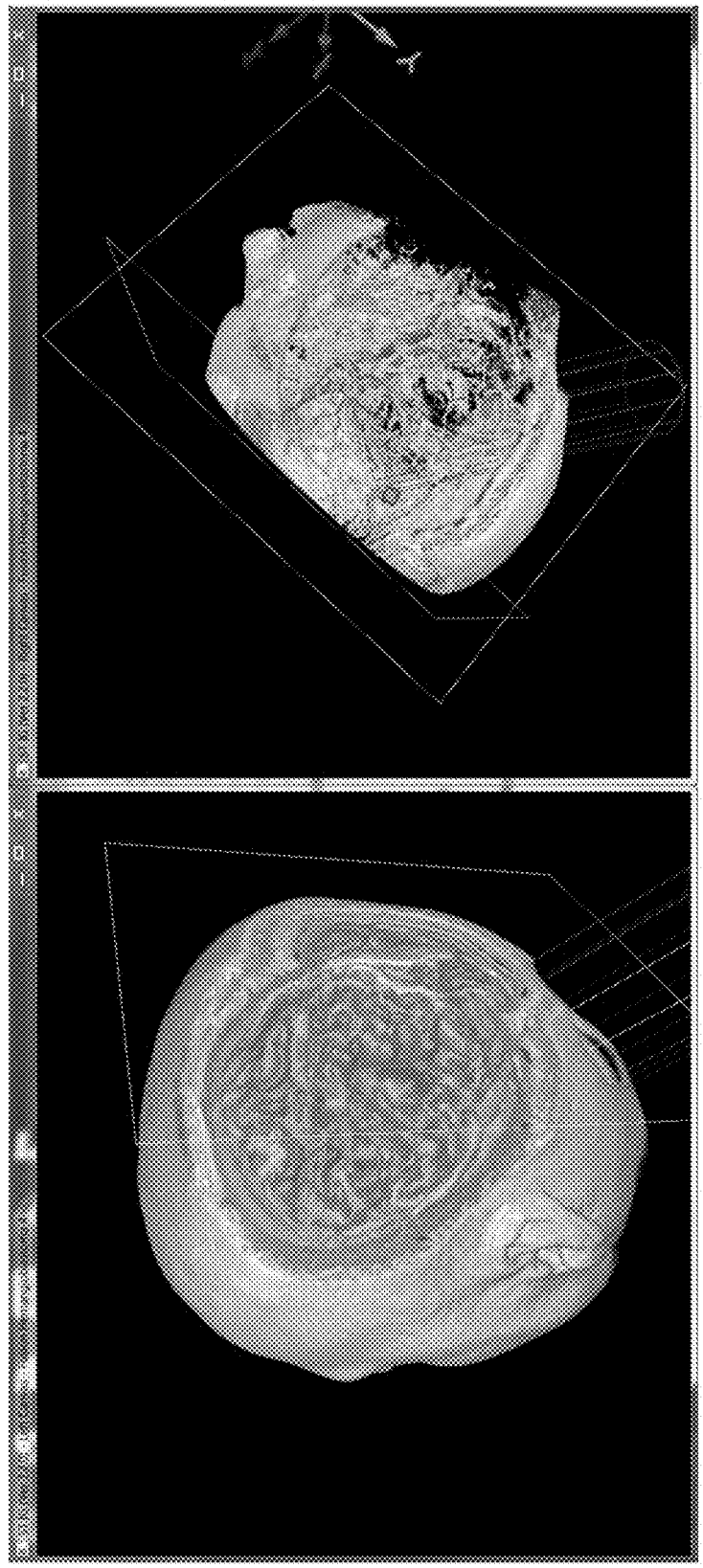

The system allows performing 'cube clipping' which trims the 3D image independently from any desired plane. The plane is defined by 2 variables—Plane normal (vector) and plane position (The point in space that the plane goes through). the "cube clipping can be perform independently for each image. FIG. 16 shows different independent clipping, whereas FIG. 17 shows different clipping on different modalities.

Figure 18:
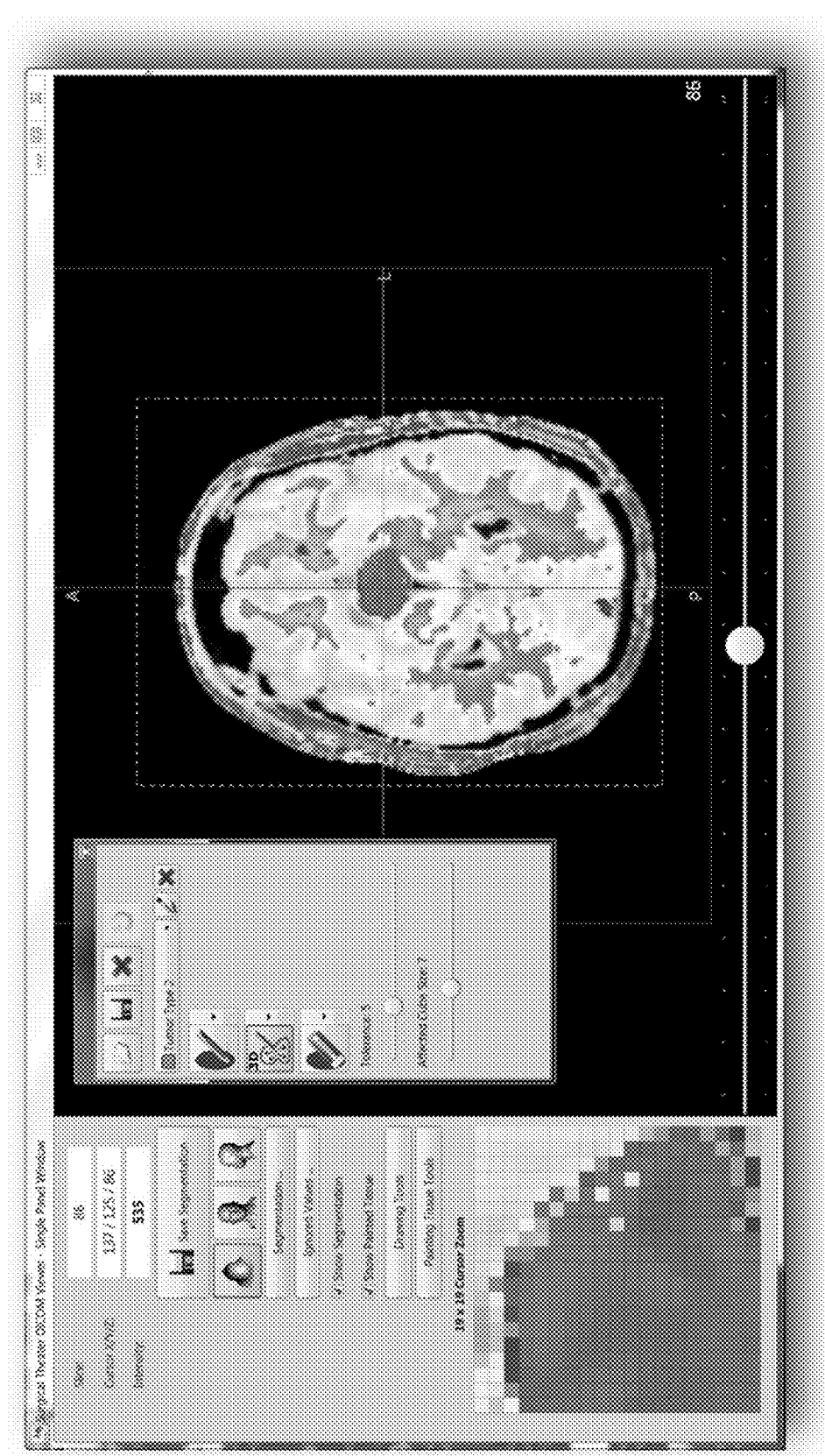

The SNAP tool has the ability to paint the tumor. For example, a surgeon can use painting during editing for case preparation and as for all the features. This can be turned on and off during the preparation or the surgery itself. FIG. 18 shows an example of painting tissue. Case Preparation" in SNAP is used to analyze and view DICOM objects residing in a folder on the local drive, and generate the 3D scene in a proprietary format to be used as input to the navigation session. This involves converting the 2D set of DICOM images to a 3D volumetric model with attributes, which is accomplished using the SNAP tool.

Measurement by virtual marking of distance in the marker pointer, placement of implants, etc. The SNAP combined modeling of implants (for example aneurysm clips or pedicle screws) and use augmented reality to guide the surgery for an accurate placement of the implements. For example, a planning of a screw placement is performed with the SNAP and the model of the screw (3D or 2D) is placed/positioned on the top of the 3D/2D model of the patient (CT, MRI etc.). Then the surgeon can navigate the real screw in the operating room and the SANP will calculate the present in the navigation the actual placement of the screw compared to the pre-planed placement. The feedback from the SANP can be provided from of an image/model of the screw that is being navigated that will turn green only when the actual placement of the screw will match the planed placement. Measurements of distance, angels, orientation etc. can be displayed in real time representing the measurements of the actual screw location and its orientation (or any other toll, implant, marker, probe in the navigation scene) with relation to the planed placement location of the screw (or any other reference point(s))

The SNAP navigation image can be rotated, shifted, zoomed etc. for each each image independently; surgeon eye view and be rotated, shifted, zoomed independently to the other image/view (for example the view form behind the pathology etc.)

Change transparency and color of each segmentation range. The SNAP allows the user to present any tissue type or element within the navigation scene in any specific color and any specific transparency.

Using SNAP

The SNAP tool can be used by a surgeon for pre-surgery preparation, and during an actual surgery. For example, SNAP can be used to support an arteriovenous malformation Nidus (Latin for "nest")—AVM Nidus.

Preparation—SNAP can be used to analyze and view DICOM objects residing in a folder on the local drive, and can be used to generate the 3D scene in a proprietary format to be used as input to a navigation session. This requires converting the 2D set of DICOM images to a 3D volumetric model with attributes. First is selected the preferable case from the library for loading it (make it the active case) and then the navigation session mode is activated by clicking the Navigation button.

Planning—the volume of interest (VOI) is defined, and the tissue deformation VOI indicates the "live" tissue that reacts realistically using the tissue's mechanical properties when interacting with a surgical tool/probe in the surgery. The Axial, Coronal and Sagittal slider controls are used to define a cube representing the tissue deformation volume of interest (VOI) to be used. Then, interaction and manipulation of the images on the SNAP's touch screen is done to plan the angles of approach and extent of exposure required to adequately visualize the draining veins and understand the location and orientation of the arterial feeders with respect to the AVM Nidus. As part of case preparation, the SNAP allows the surgeon to use the image generator to display a Volume of Interest (VOI) window to define an image, such as for defining a tissue deformation volume to be used for simulation. A button then allows the surgeon to display the VOI window to define characteristics of the VOI.

Axial, Coronal and Sagittal slider controls are provided in SNAP to define a cube representing the volume of interest (VOI) to be used by Surgery Simulation application. Adjusting the high and low boundary Axial sliders define the top and bottom boundaries for the VOI. Adjusting the high and low boundary Coronal sliders define the front and back boundaries for the VOI. Adjusting the high and low boundary Sagittal sliders define the left and right side boundaries for the VOI. The sliders values for each axis are provided in High and Low Boundary fields.

Visualizing—The Tissue Segmentation Window can be used to modify tissue-specific intensity ranges applied to the patient data. Either the Tissue Rendering Thresholds (Segmentation Defaults) feature can be used, or the segmentation can be modified. By doing this one can adjust and customize the segmentation to highlight the AVM Nidus, the draining veins, feeding arteries and the transverse sinuses for optimal visualization, while making the skull and less vital structures more transparent.

3D Navigating—SNAP can be integrated with a traditional navigation system where one can review simultaneously the trajectory on the 2D set of DICOM images (on the traditional navigation system) and on the 3D volumetric model (on the SNAP). With SNAP the surgeon is able to navigate using the 3D angiogram and accurately target the non-embolized feeding arteries at the superior surface of the AVM Nidus.

Example Application

As discussed above, SNAP can be used in a surgical environment for supporting a surgical operation on a patient. Here, we provide one example scenario to exemplify its use for a craniotomy of an example patient with a cranial tumor.

The surgeon creates and updates a patient case by feeding set-up parameters of his patient which include details of the patient that allow the system to up-load the relevant data for the particular patient, the SNAP then loads the patient's CT, CTA, MRI and MRA imageries and other information that concern the simulated models, such as patient age, gender and so on.

The surgeon will see on the traditional navigation system three planes, which would be the axial, the crown and the sagittal plan and at the same time on the SNAP display the surgeon will see the three dimensional imagery of the same patient head. Hence, the SNAP display shows greater detail in a more realistic looking manner.

The surgeon activates the navigation session mode by clicking the Navigation button on the SNAP touchscreen. The system displays the navigation session windows—Two independent IG camera windows (canvas) and the navigation quick window.

The surgeon will go to the fusion mode where he SNAP will show the combined model where the CTA overlaid the MRI and will define the working mode for example he will select the combined mode where both layers (CTA and MRI) displayed on both canvasses.

Now the surgeon will Use the transparency preset buttons and the left/right buttons on the dialog window of the display to set the desired transparency level for the layers (CTA and the MRI).

On the left canvas the surgeon will select one of four transfer functions. He will start changing the transparency by moving the "keys" on the transfer function dialog window. For changing the "keys" he will use the system mouse. The surgeon will manipulate the "keys" until he will get the desirable look for example the one that you can see the tumor, his boundaries and the veins.

On the right canvas the surgeon will select a different transfer function, which, for example, he can see the important landmarks.

By touching the SNAP screen to turn the model left and right and doing zoom in and zoom out, the surgeon gets a better representation of the tumor in three-dimensional space and can determine about how big are bony opening is going to have to be. The surgeon can really truly understand what the relationship of the tumor is to where the blood vessels are and how he is going to be approaching the tumor in the operation.

The surgeon will mark the important veins and the desired bony opening on the skull bone using the SNAP tool.

The surgeon will use the SNAP navigation pointer to estimate the path length from the skull to the tumor. He will put the tip of the pointer on the penetration point on the skull and will select on the SNAP tool the virtual trajectory pointer from the navigation pointer type menu.

On the SNAP display, the surgeon will see the pointer with the trajectory extension moving on real time according to his movement. By giving the suitable direction, he will obtain the penetration length.

The surgeon has the option to freeze the data from the navigation system. In this case, incoming data is ignored and the pointer stays at its last position prior to clicking the freeze button. The surgeon will use SNAP to turn the model left and right and zooming in and out and he will get a better representation of the path and the vital parts around.

Next, the surgeon will start the craniotomy according to the information he saw on the SNAP. After opening the craniotomy the surgeon start to cut throw the path and by using the navigation pointer he can follow on the SNAP that he is on the right path, he can estimate the distance to the tumor and how close he is to the sinuses and veins.

Example of Using the Proximity Application

Path is created to navigate toward a tumor though a keyhole craniotomy. The keyhole craniotomy is mall and doesn't allow the surgeon see much of the structures. Therefore, a path or trajectory to the target (tumor) is created. Additionally, Markers or Paths will be crafted to mark areas to avoid.

During the surgery, the SNAP presents a real time 3D and 2D image of the navigation scene which shows the surgeon his tools location, the surgeon can follow the navigation path. The surgeon can also modify his Path, marks, Trajectories etc. The modification is done in a similar way that the Markers, Targets etc. where catered: Markers, Targets etc. can be dragged to a different location, recolored etc.

During the navigation, should the surgeon deviate from a specific Marker, Path, Trajectory etc. by a specific preset value (distance, angel, etc.) a warning will go off. The specific preset value (distance, angel, etc.) can be modified.

Example for Guidance of catheter rowed 3rd Ventriculostomy target.—Surgeon Mark a point in the 3rd Ventriculostomy as a Target. The surgeon mark Entry point. The SNAP creates a Trajectory and visual graphics to guide the surgeon form the catheter placement.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. A modeling system for performing a medical procedure on a particular patient, comprising:
    a display;
    a database for storing a library of a plurality of models of different organs and/or tissues;
    an image generator including specialized software executing on a computer system for generating a dynamic image model of biological tissues for display, said generating for displaying the tissues realistically representing corresponding actual biological tissues of a particular patient;
    a user navigation interface including specialized software executing on the computer system to generate a navigation path for the medical procedure in the dynamic image model;
    a camera for generating a live image of the biological tissues of the particular patient for display;
    a user tool generator including specialized software executing on a computer system for generating a tool model of a user tool for dynamically interacting with said dynamic image of said biological tissues via manipulations provided by a user input for display;
    a user interface for selecting one model from said plurality of models for use with said user tool model for dynamically interacting with said image of tissues; and
    a user interface to the computer system configured for permitting a user to adjust the dynamic image of said biological tissues for display during the medical procedure by adding or modifying features of said biological tissues utilizing images obtained from both the dynamic image model and live images to provide a combined image for display on said display to aid implementation of the medical procedure on the particular patient, wherein said modeling system is configured to accept a settable deviation amount value, and wherein said modeling system is configured for use in an operating room during the medical procedure on the particular patient to track activity during implementation of the medical procedure for detecting a deviation from said navigation path by the set deviation amount value such that an alarm is activated by the modeling system in response to the detected deviation from said navigation path during the implementation of the medical procedure.

2. The modeling system of claim 1, wherein the user interface to adjust the dynamic image of tissues includes a tool to provide the ability to draw any geometric shape on the dynamic image of tissues.

3. The modeling system of claim 1, wherein the user interface to adjust the dynamic image of tissues includes a tool to provide the ability to complete an incomplete anatomical structure of the dynamic image of tissues.

4. The modeling system of claim 1, wherein the user interface to adjust the dynamic image of tissues provides the ability to modify the texture, lighting, shadow and/or shading of a portion of the dynamic image of tissues.

5. The modeling system of claim 1, wherein said dynamic image of tissues include an image of an anatomical structure and wherein said user interface includes an instrument for dynamically interacting with the anatomical structure.

6. The modeling system of claim 1, wherein the user interface to adjust the dynamic image of tissues includes a real surgical tool being used by a surgeon to perform a surgery on the particular patient.

7. The modeling system of claim 1, wherein the user interface to adjust the dynamic image of tissues includes a tool to provide the ability to select elements of a model of the tool and/or the dynamic image of tissues for removal from the displayed image.

8. The modeling system of claim 1, wherein the user interface to adjust the dynamic image of tissues includes a tool to provide the ability to reposition or rotate objects in the displayed image by selecting the objects and manipulating the objects to a desired position for display in the image.

9. The modeling system of claim 1, wherein the user interface to adjust the dynamic image of tissues includes a tool to provide the ability to enhance and integrate anatomical structure in the dynamic image.

10. The modeling system of claim 1, wherein the user interface to adjust the dynamic image of tissues includes a tool to provide the ability to a draw any geometric shape for adding to the dynamic image of tissues.

11. The modeling system of claim 1, wherein said modeling system is configured with an interface to connect to an interface of an external surgical system present in an operating room for receiving data from the external surgical system for use in generating said dynamic image of tissues for display consistent with an operation of the external surgical system.

12. The modeling system of claim 11, wherein said external surgical system is a navigation system for use during the medical procedure which is a surgical procedure being performed in the operating room.

13. The modeling system claim 1, wherein said modeling system is configured to provide a warning to the surgeon about a proximity of one or more surgical tools to a specific anatomical structure of the patient.

14. The modeling system of claim 1, wherein said surgical path includes the user placing a marker marking a specific anatomical structure of the particular patient, and wherein the alarm is activated by the modeling system when the surgeon deviates from said navigation path during the implementation of the medical procedure by a proximity of the user tool to the specific anatomical structure represented by the marker during the surgery.

15. A method of using a modeling system to support a medical procedure, comprising the steps of:
providing a computer system configured for use in an operating room;
providing at least one display connected to said computer system;
obtaining patient image information about the biological tissues of a particular patient for storing in said computer system;
generating, using specialized software executing on the computer system, a dynamic image model of the biological tissues of the particular patient for display, said generating utilizing said patient image information such that said dynamic image of tissues is displayed realistically representing corresponding actual tissues of the particular patient;
generating, using specialized software executing on the computer system, a user navigation interface to generate a navigation path for the medical procedure in the dynamic image model;
providing a camera in said operating room for generating a live image of the biological tissues of the particular patient;
generating, using specialized software executing on the computer system, a user tool model for dynamically interacting with said dynamic image of tissues via manipulations input by a user for display, wherein the computer system comprises a database for storing a library of a plurality of models of different organs and/or tissues, and a user interface for selecting one model from said plurality of models for use with said user tool model for dynamically interacting with said image of tissues;
adjusting, using a user input to said computer system during the medical procedure, the dynamic image of tissues displayed on the at least one display by adding or modifying features of said biological tissues using images obtained from both the dynamic image model and the live images to provide a combined image of the biological tissues of the particular patient for display on the at least one display;
generating, using the computer system, a realistic simulation of at least a part of the surgical procedure being performed on the particular patient for display on the at least one display showing dynamic interactions using the combined image; accepting a settable deviation amount value as an input to said computer system; and tracking activity during implementation of the medical procedure on the particular patient to detect a deviation of said activity from said navigation path by said deviation amount value such that an alarm is activated by the computer system for the detected deviation from said navigation path during the implementation of the medical procedure.

16. The method of claim 15, wherein said user tool model includes a model of an actual surgical tool being used by a surgeon during performing the medical procedure including a surgery on the particular patient.

17. The method of claim 16, wherein said user tool model includes an image collecting tool configured for receiving an image of tissues of the particular patient, such that by manipulating the image collecting tool, the images displayed on the display are modified.

18. The method of claim 15, wherein said adjusting includes painting at least a portion of the image of tissues.

19. The method of claim 15, wherein said adjusting includes making at least a portion of the image of tissues transparent.

20. The method of claim 15, wherein said adjusting includes rotating an image on the display.

21. The method of claim 15, further comprising the step of building a case to support the medical procedure in advance of said medical procedure by creating models for the particular patient using patient medical images configured for generating said dynamic image of the biological tissues of the particular patient.

22. The method of claim 15, further comprising the step of receiving data from an external surgical system being used by the surgeon, said data being used by said simulation tool to ensure that said dynamic image of the biological tissues is consistent with an operation of the external surgical system.

23. The method of claim 15, further comprising the step of receiving data from a surgical navigation system being used for the medical procedure which is a surgery on the particular patient for use in generating said dynamic image of the biological tissues consistent with an operation of the surgical navigation system.

24. The method of claim 15, further comprising the step of warning the user about a proximity of one or more surgical tools to a specific anatomical structure of the patient.

25. The modeling system claim 15, wherein said modeling system is configured to provide a warning to the surgeon about a proximity of one or more surgical tools to a specific anatomical structure of the patient.

26. A method of using a modeling system to support a surgery, comprising the steps of:
providing a computer system configured for use in an operating room; providing at least one 3D display connected to said computer system;
obtaining patient image information about the biological tissues of a particular patient;
building a case to support said surgery in advance of said surgery by creating models for the particular patient using the patient medical images configured for generating dynamic images of the biological tissues of the particular patient;

generating, using specialized software executing on the computer system, the dynamic images of the biological tissues of the particular patient for display on at least one display using said models, said generating utilizing said patient image information such that said dynamic image of tissues is displayed on said display realistically represent corresponding actual tissues of the particular patient;

providing a camera in said operating room for generating a live image of the biological tissues of the particular patient;

during the surgery generating, using said computer system, a user tool model for dynamically interacting with said dynamic image of tissues via manipulations input by a user for display, wherein the computer system comprises a database for storing a library of a plurality of models of different organs and/or tissues; and a user interface for selecting one model from said plurality of models for use with said user tool model for dynamically interacting with said image of tissues;

generating, using specialized software executing on the computer system, a user navigation interface to generate a navigation path for the surgery in the dynamic image model, said navigation path including placement of a marker marking a specific anatomical structure of the particular patient; adjusting, using a user input to said computer system, the dynamic image of tissues displayed on the at least one display by adding or modifying features of said biological tissues of images obtained from said models combined with live images of said biological tissues for display to show anatomical structures that are in the actual biological tissue of the particular patient;

generating, using the computer system, a realistic simulation of at least a part of the actual surgical procedure being performed on the particular patient for display on said display showing interactions between the dynamic image of tissues as combined and the user tool model according to inputs by the user; receiving data from an external surgical system being used during the surgery, said data being used by said simulation tool to ensure that said dynamic image of the biological tissues is consistent with an operation of the external surgical system; accepting a settable deviation amount value as an input to said surgical system; and providing a capability of warning the user about a proximity within the set deviation amount of one or more surgical tools to the specific anatomical structure represented by the marker marking the specific anatomical structure of the patient during the surgery.

27. The method of claim 26, wherein said adjusting includes painting at least a portion of the image of tissues, making at least a portion of the image of tissues transparent, and/or rotating an image on the display.

28. A modeling system for performing a surgical procedure, comprising:

at lease one touchscreen display;

a database for storing a library of a plurality of models of different organs and/or tissues, wherein said database is also configured for storing medical images of a particular patient, and wherein said modeling system is configured for building a case to support said surgical procedure in advance of said procedure by creating models for the particular patient using the patient medical images, said models for providing a simulation of the surgical procedure via said modeling system, wherein said models include provision of a navigation path for performing said surgical procedure on the particular patient;

a user interface generated by said computer system for selecting said case from a plurality of such cases for loading in said modeling system;

an image generator including specialized software executing on a computer system for generating a dynamic image of tissues for display on the at least one touchscreen display based on said selected case models, said generating for displaying the tissues realistically representing corresponding actual biological tissues of the particular patient; a camera for generating a live image of the biological tissues particular patient for display; a user tool generator including specialized software executing on a computer system for generating a tool model of a user tool for dynamically interacting with said dynamic image of tissues via manipulations provided by a user input for display on the at least one display;

a user interface for selecting one model from said plurality of models for use with said user tool model for dynamically interacting with said image of tissues;

a user interface to the computer system configured for receiving inputs from the user for configuring the modeling system via said at least one touchscreen display to generate a combined dynamic image of the biological tissues using images of the biological tissue from the selected case models combined with live images of the biological tissue for display on the at least one touchscreen display; and an interface to connect to an interface of an external surgical system or tool present in the operating room for receiving data from the external surgical system or tool for use in generating said combined dynamic image of said biological tissues for display consistent with an operation of the external surgical system or tool, wherein said modeling system is configured to accept a settable deviation amount value, and wherein said modeling system detects, during the surgical procedure, a deviation from said navigation path by the set deviation amount value, and wherein said modeling system is configured for use in an operating room during actual performance of the surgical procedure on the particular patient such that an alarm is activated by the modeling system when a part of the implementation of the surgical procedure detected a deviation from said navigation path during the implementation of the medical procedure on the particular patient.

* * * * *